(12) United States Patent
Sirizzotti et al.

(10) Patent No.: US 11,963,496 B2
(45) Date of Patent: Apr. 23, 2024

(54) WATERMELON VARIETY NUN 11802 WMW

(71) Applicant: Nunhems B.V., Nunhem (NL)

(72) Inventors: Alberto Sirizzotti, Sant Agata Bolognese (IT); Elena Chiapparino, Sant Agata Bolognese (IT)

(73) Assignee: NUNHEMS B.V., Nunhem (NL)

( * ) Notice: Subject to any disclaimer, the term of this patent is extended or adjusted under 35 U.S.C. 154(b) by 23 days.

(21) Appl. No.: 17/556,335

(22) Filed: Dec. 20, 2021

(65) Prior Publication Data

US 2022/0110280 A1    Apr. 14, 2022

(30) Foreign Application Priority Data

Dec. 21, 2020   (AU) .............................. 2020904758

(51) Int. Cl.
*A01H 5/08*    (2018.01)
*A01H 1/00*    (2006.01)
*A01H 6/34*    (2018.01)

(52) U.S. Cl.
CPC .............. *A01H 6/342* (2018.05); *A01H 1/00* (2013.01); *A01H 5/08* (2013.01)

(58) Field of Classification Search
None
See application file for complete search history.

(56) References Cited

U.S. PATENT DOCUMENTS

| | | | |
|---|---|---|---|
| 8,418,637 | B2 | 4/2013 | Gill et al. |
| 2006/0168701 | A1 | 7/2006 | Zhang et al. |
| 2015/0126380 | A1 | 5/2015 | Van Dun |
| 2015/0245570 | A1 | 9/2015 | Vogelaar et al. |
| 2019/0343063 | A1* | 11/2019 | Chang ...................... A01H 5/08 |

OTHER PUBLICATIONS

"DUS Test for Watermelon—*Citrullus lanatus* (Thunb.) Matsum. et Nakai.", Calibration Manual—Harmonized with Naktuinbouw and NCSS (/NARO), Aug. 28, 2017, 51 pages.
"Guidelines for the Conduct of Tests for Distinctness, Uniformity and Stability", UPOV, International Union for the protection of new variety of plants, Geneva, UPOV Code: CTRLS_LAN (Citrullus lanatus (Thunb.) Matsum. et Nakai), TG/142/5, Oct. 29, 2019, 39 pages.
"Objective Description of Variety Watermelon (*Citrullus lanatus* (Thunb.) Matsum. & Nakai)", US Department of Agriculture, Agricultural Marketing Service Science and Technology Plant Variety protection office, 2015, 4 pages.
Baameur, et al., "Watermelon Production in California", University of California, Division of Agriculture and Natural Resources, Publication 7213, 2009, 5 pages.
Compton, et al., "Use of Tissue Culture and Biotechnology for the Genetic Improvement of Watermelon", Plant Cell, Tissue and Organ Culture, vol. 77, Issue 3, Jun. 2004, pp. 231-243.
Hayata, et al., "Synthetic Cytokinin-1-(2=chloro=4=pyridyl)-3-phenylurea (CPPU)—Promotes Fruit Set and Induces Parthenocarpy in Watermelon", Society for Horticultural Science, vol. 120, Issue 6, Nov. 1995, pp. 997-1000.
Hitoshi Kihara ,"Triploid watermelons", Proceedings of the American Society for Horticultural Science, vol. 58, 1951, pp. 217-230.
Moussa, et al., "Parthenocarpy of watermelon cultivars induced by γ-irradiation", Russian Journal of Plant Physiology, vol. 57, Issue 4, Jul. 2010, pp. 574-581.
Needleman, et al., "A general method applicable to the search for similarities in the amino acid sequence of two proteins", Journal of Molecular Biology, vol. 48, Issue 3, Mar. 28, 1970, pp. 443-453.
Nikolova, et al., "Diploidization of cucumber (*Cucumis sativus* L.) haploids by colchicine treatment", Acta Societatis Botanicorum Poloniae, vol. 65, Issue 3-4, 1996, pp. 311-317.
O.J. Eigsti, "About our cover", HortScience, vol. 6, 1971, 1 page.
Parvathaneni, et al., "Fingerprinting in cucumber and melon (*Cucumis* spp.) Genotypes using morphological and SSR markers", Journal of Crop Science and Biotechnology, vol. 14, Issue 1, Mar. 2011, pp. 39-43.
Rice, et al., "EMBOSS: the European Molecular Biology Open Software Suite", Trends in Genetics, vol. 16, Issue 6, Jun. 2000, pp. 276-277.
Robert W. Allard, "Overview of Plant Breeding", Principles of Plant Breeding, 2nd Edition, May 26, 1999, pp. 64-67.
Songstad, et al., "Genome Editing of Plants", Critical Reviews on Plant Science, vol. 36, Issue 1, Mar. 8, 2017, pp. 1-23.
Vidavsky, et al., "Tomato Breeding Lines Resistant and Tolerant to Tomato Yellow Leaf Curl Virus Issued from Lycopersicon hirsutum", Phytopathology, vol. 88, Issue 9, Sep. 1998, pp. 910-914.
Vos, et al., "AFLP: a new technique for DNA fingerprinting", Nucleic Acids Research, vol. 23, Issue 21, Nov. 11, 1995, pp. 4407-4414.
Wijnker, et al., "Hybrid recreation by reverse breeding in *Arabidopsis thaliana*", Nature Protocols, vol. 9, 2014, pp. 761-772.

* cited by examiner

*Primary Examiner* — Phuong T Bui
(74) *Attorney, Agent, or Firm* — ArentFox Schiff LLP

(57) ABSTRACT

A new and distinct watermelon variety NUN 11802 WMW is disclosed as well as seeds and plants and fruits thereof. NUN 11802 is a round oval, diploid watermelon variety of the mini-seeded type, comprising resistance to *Fusarium oxysporum* f. s.p *niveum* Race 0 and Race 1.

32 Claims, 6 Drawing Sheets

WATERMELON VARIETY NUN 11802 WMW

CROSS-REFERENCE TO RELATED APPLICATION

This application claims priority to Australian Provisional Application No. 2020/904,758 filed on Dec. 21, 2020, which is hereby incorporated by reference in its entirety.

FIELD OF THE DISCLOSURE

The disclosure relates to the field of plant breeding and, more specifically, to watermelon variety NUN 11802 WMW. The disclosure further relates to vegetative reproductions of watermelon variety NUN 11802 WMW, methods for tissue culture of watermelon variety NUN 11802 WMW and regenerating a plant from such a tissue culture and to phenotypic variants of watermelon variety NUN 11802 WMW. The disclosure also relates to progeny of watermelon variety NUN 11802 WMW and the hybrid varieties obtained by crossing watermelon variety NUN 11802 WMW as a parent line with plants of other varieties or parent lines.

BACKGROUND OF THE DISCLOSURE

The goal of plant breeding is to combine various desirable traits in a single variety. Such desirable traits may include greater yield, resistance to diseases, insects or other pests, tolerance to heat and drought, better agronomic quality, higher nutritional value, enhanced growth rate, and improved fruit properties.

Breeding techniques take advantage of a plant's method of pollination. There are two general methods of pollination: a plant self-pollinates if pollen from one flower is transferred to the same or another flower of the same genotype. A plant cross-pollinates if pollen comes to it from a flower of a different genotype. Plants that have been self-pollinated and selected for (uniform) type over many generations become homozygous at almost all gene loci and produce a uniform population of true breeding progeny of homozygous plants. A cross between two such homozygous plants of different lines produces a uniform population of hybrid plants that are heterozygous for many gene loci. The extent of heterozygosity in the hybrid is a function of the genetic distance between the parents. Conversely, a cross of two plants each heterozygous at a number of loci produces a segregating population of hybrid plants that differ genetically and are not uniform. The resulting non-uniformity makes performance unpredictable.

The development of uniform varieties requires the development of homozygous inbred plants, the crossing of these inbred plants to make hybrids, and the evaluation of the hybrids resulting from the crosses. Pedigree breeding and recurrent selection are examples of breeding methods that have been used to develop inbred plants from breeding populations. Those breeding methods combine the genetic backgrounds from two or more plants or various other broad-based sources into breeding pools from which new lines are developed by selfing and selection of desired phenotypes. The new plants are evaluated to determine which have commercial potential.

One valuable crop that has been subject to breeding programs is watermelon, a member of the Cucurbitacea family. The genus *Citrullus* originated in Africa. The plant is a large and sprawling annual, grown for its fruit. The fruit of watermelon is often colored attractively, commonly red. Watermelon can contain black seeds, which are considered undesirable for certain uses. Watermelon is primarily consumed fresh. The fruit can be eaten fresh as dessert, snack, salad, or juice. Watermelon is also processed to produce roasted seeds, pickled rind, pickled fruit, or powdered juice.

Watermelon (*Citrullus lanatus*) can occur as a diploid, triploid, or tetraploid. Seedless watermelon fruits are produced by using pollen from diploid male parent plants to fertilize flowers of tetraploid maternal parent plants. Pollination of the tetraploid flowers with diploid pollen leads to hybrid F1 seeds which are triploid (see, e.g., Kihara, 1951, Proceedings of American Society for Horticultural Science 58: 217-230; Eigsti 1971, Hort Science 6: 1-2). The triploid hybrid plants grown from these F1 seeds are self-infertile as they produce sterile pollen due to chromosome imbalance and need to be pollinated by a diploid pollenizer to produce watermelon fruit. Triploid plants are, therefore, interplanted with pollenizer plants for fruit production. The "seedless" fruit produced after pollination on the triploid hybrid plant are not truly seedless, but often contain some undeveloped, small, pale seeds, which are edible. Plants are generally planted at a ratio of 1 pollenizer per every 2-4 triploid plants. Triploid plants and pollenizers are either planted in separate rows (e.g., 1 row of pollenizer and 2-4 rows of triploids), or interplanted within rows (e.g., planting 1 pollenizer plant in between 2 to 3 triploid plants in the same row), or interplanted in narrow rows between rows of triploids (see, e.g., Table 2 of US2006/0168701 and U.S. Pat. No. 8,418,637, which is herein incorporated by reference in their entireties). The fruit produced on the pollenizer plants preferably has a different rind pattern from the fruit on the triploid hybrids, so that these can be easily distinguished.

Grading of fruits is usually done by fruit weight, to distinguish "mini" watermelons, with weights of less than 6 pounds (2.72 kg), "icebox" watermelons with weights of 8-12 pounds (3.62 kg-5.44 kg) or, according to others, of 6 to 15 pounds (2.72 kg to 6.8 kg) and "picnic" watermelons of above the icebox size, so either above 12 pounds (above 5.44 kg) or above 15 pounds (above 6.8 kg). Furthermore, watermelon fruit flesh can have various colors, including various tints of red, pink, orange, and yellow.

Watermelons are produced across the United States with the most volume of production coming from Texas, Florida, Georgia, and California. The consumer demand for watermelon, in particular for seedless (triploid) varieties is continuously growing due to its health benefits. This translates to an increased demand for improved watermelon varieties of different sizes, shapes, and fruit quality. Other objectives include varying the color, texture, and flavor of the fruit, absence of seeds, disease or pest resistance, optimizing flesh thickness, yield, suitability to various climatic circumstances, solid content (% dry matter), and sugar content.

SUMMARY OF THE VARIOUS ASPECTS OF THE DISCLOSURE

The disclosure provides for watermelon variety NUN 11802 WMW, products thereof, and methods of using the same. NUN 11802 is a round oval, diploid watermelon variety of the mini-seeded type and is suitable for growing in the open field.

In another aspect, the plant of watermelon variety NUN 11802 WMW or part thereof or progeny thereof comprises resistance to *Fusarium oxysporum* f. s.p *niveum* Race 0 and Race 1, measured according to UPOV standards described in TG/142/5.

The disclosure also provides a watermelon plant or part thereof having all of the physiological and morphological characteristics of the plant of watermelon variety NUN 11802 WMW when grown under the same environmental conditions.

In another aspect, the plant of variety NUN 11802 WMW or progeny thereof has 18, 19, or more or all of the following distinguishing characteristics when compared to the Reference Variety as shown in Table 4: 1) round small fruit type; 2) larger stem diameter; 3) shorter leaf length; 4) narrower leaf width; 5) grey green leaf color; 6) shorter petiole length; 7) smaller petiole width; 8) shorter fruit length; 9) smaller fruit diameter; 10) lighter fruit weight; 11) lighter yellow green primary color (ground color); 12) dark grey green secondary color (stripes); 13) broad elliptic fruit shape in longitudinal section; 14) weaker conspicuousness of veining; 15) one colored and marbled pattern of stripes; 16) shorter peduncle length; 17) smaller peduncle width; 18) smaller stem end thickness; 19) lower % soluble solids, when determined at 5% significance level for numerical characteristics and determined by type or degree for non-numerical characteristics for plants grown under the same environmental conditions.

The disclosure also provides for a progeny of watermelon variety NUN 11802 WMW. In another aspect, the disclosure provides a plant or a progeny retaining all or all but one, two, or three of the "distinguishing characteristics" or all or all but one, two or three of the "morphological and physiological characteristics" of watermelon variety NUN 11802 WMW and methods for producing that plant or progeny.

In another aspect, the disclosure provides a plant or a progeny having all the physiological and morphological characteristics of watermelon variety NUN 11802 WMW when grown under the same environmental conditions. In another aspect, the plant or progeny has all or all but one, two, or three of the physiological and morphological characteristics of watermelon variety NUN 11802 WMW when measured under the same environmental conditions and e.g., evaluated at significance levels of 1%, 5%, or 10% significance (which can also be expressed as a p-value) for quantitative characteristics and determined by type or degree for non-quantitative characteristics, wherein a representative sample of seed of watermelon variety NUN 11802 WMW has been deposited under Accession Number NCIMB 43701. In another aspect, the plant or progeny has all or all but one, two, or three of the physiological and morphological characteristics as listed in Tables 1-3 for watermelon variety NUN 11802 WMW when measured under the same environmental conditions and e.g., evaluated at significance levels of 1%, 5%, or 10% significance (which can also be expressed as a p-value) for quantitative characteristics and determined by type or degree for non-quantitative characteristics.

In another aspect, the disclosure provides a seed of watermelon variety NUN 11802 WMW, wherein a representative sample of said seed has been deposited under Accession Number NCIMB 43701. The disclosure also provides for a plurality of seeds of watermelon variety NUN 11802 WMW. The watermelon seed of variety NUN 11802 WMW may be provided as an essentially homogeneous population of watermelon seed. The population of seed of variety NUN 11802 WMW may be particularly defined as essentially free from other seed. The seed population may be grown into plants to provide an essentially homogeneous population of watermelon plants as described herein.

The disclosure also provides a plant grown from a seed of watermelon variety NUN 11802 WMW and plant part thereof.

The disclosure further provides a watermelon fruit produced on a plant grown from a seed of watermelon variety NUN 11802 WMW.

In another aspect, the disclosure provides a seed growing or grown on a plant of variety NUN 11802 WMW (i.e., produced after pollination of the flower of watermelon variety NUN 11802 WMW).

In another aspect, the disclosure provides for a plant part obtained from watermelon variety NUN 11802 WMW, wherein said plant part is: a fruit, a harvested fruit, a part of a fruit, a leaf, a part of a leaf, pollen, an ovule, a cell, a petiole, a shoot or a part thereof, a stem or a part thereof, a root or a part thereof, a root tip, a cutting, a seed, a part of a seed, seed coat or another maternal tissue which is part of a seed grown on said variety, a hypocotyl, a cotyledon, a scion, a stock, a rootstock, a pistil, an anther, or a flower or a part thereof. Fruits are particularly important plant parts. Such plant parts may be suitable for sexual reproduction, vegetative reproduction, or a tissue culture. In another aspect, the plant part obtained from variety NUN 11802 WMW is a cell, optionally a cell in a cell or tissue culture. That cell may be grown into a plant of variety NUN 11802 WMW.

In another aspect, the disclosure provides for a hybrid watermelon variety NUN 11802 WMW.

The disclosure also provides a cell culture of watermelon variety NUN 11802 WMW and a plant regenerated from watermelon variety NUN 11802 WMW, which plant has all the characteristics of watermelon variety NUN 11802 WMW when grown under the same environmental conditions, as well as methods for culturing and regenerating watermelon variety NUN 11802 WMW. Alternatively, a regenerated plant may have one characteristic that is different from watermelon variety NUN 11802 WMW.

The disclosure further provides a vegetatively propagated plant of variety NUN 11802 WMW having all or all but one, two or three of the morphological and physiological characteristics of watermelon variety NUN 11802 WMW when grown under the same environmental conditions as well as methods for vegetatively propagating watermelon variety NUN 11802 WMW.

In another aspect, the disclosure provides a method of producing a watermelon plant comprising crossing watermelon variety NUN 11802 WMW with itself or with another watermelon variety and selecting a progeny watermelon plant from said crossing.

The disclosure also provides a method of producing a melon plant derived from watermelon variety NUN 11802 WMW.

In further aspect, the disclosure provides a method of producing a hybrid watermelon seed comprising crossing a first parent watermelon plant with a second parent watermelon plant and harvesting the resultant hybrid watermelon seed, wherein said first parent plant or second parent watermelon plant is watermelon variety NUN 11802 WMW. Also provided is a hybrid watermelon seed produced from crossing a first parent watermelon plant and second parent watermelon plant and harvesting the resultant hybrid watermelon seed, wherein said first parent plant or second parent watermelon plant is watermelon variety NUN 11802 WMW. Moreover, the hybrid watermelon plant grown from the hybrid watermelon seed is provided.

In another aspect, the disclosure provides a method of introducing a single locus conversion into the plant of variety NUN 11802 WMW, wherein a representative sample of seed of said watermelon variety has been deposited under Accession Number NCIMB 43701, wherein the plant comprises the single locus conversion and otherwise has all of the physiological and morphological characteristics of watermelon variety NUN 11802 WMW.

In yet another aspect, the disclosure provides a method for introducing a desired trait into watermelon variety NUN 11802 WMW, said method comprises transforming the plant of variety NUN 11802 WMW with a transgene that confers the desired trait, wherein the plant contains the desired trait and otherwise has all of the physiological and morphological characteristics of watermelon variety NUN 11802 WMW.

The disclosure also provides a method of producing a modified watermelon plant with a desired trait, wherein the method comprises mutating a watermelon plant or plant part of watermelon variety NUN 11802 WMW, wherein a representative sample of seed of said watermelon variety has been deposited under Accession Number NCIMB 43701, and wherein the mutated plant contains the desired trait and otherwise has all of the physiological and morphological characteristics of watermelon variety NUN 11802 WMW.

In one aspect, the single locus conversion or desired trait is yield, storage properties, color, flavor, size, firmness, enhanced nutritional quality, post-harvest quality, male sterility, herbicide tolerance, insect resistance, pest resistance, disease resistance, environmental stress tolerance, modified carbohydrate metabolism, modified protein metabolism, or ripening.

In another aspect, the disclosure provides a container comprising the plant, plant part, or seed of watermelon variety NUN 11802 WMW.

Also provided is a food, a feed, or a processed product comprising a plant part of watermelon variety NUN 11802 WMW, wherein the plant part is a fruit or part thereof.

DEFINITIONS

Figure 1:
FIG. 1 shows the fruit of watermelon variety NUN 11802 WMW.
Figure 2:
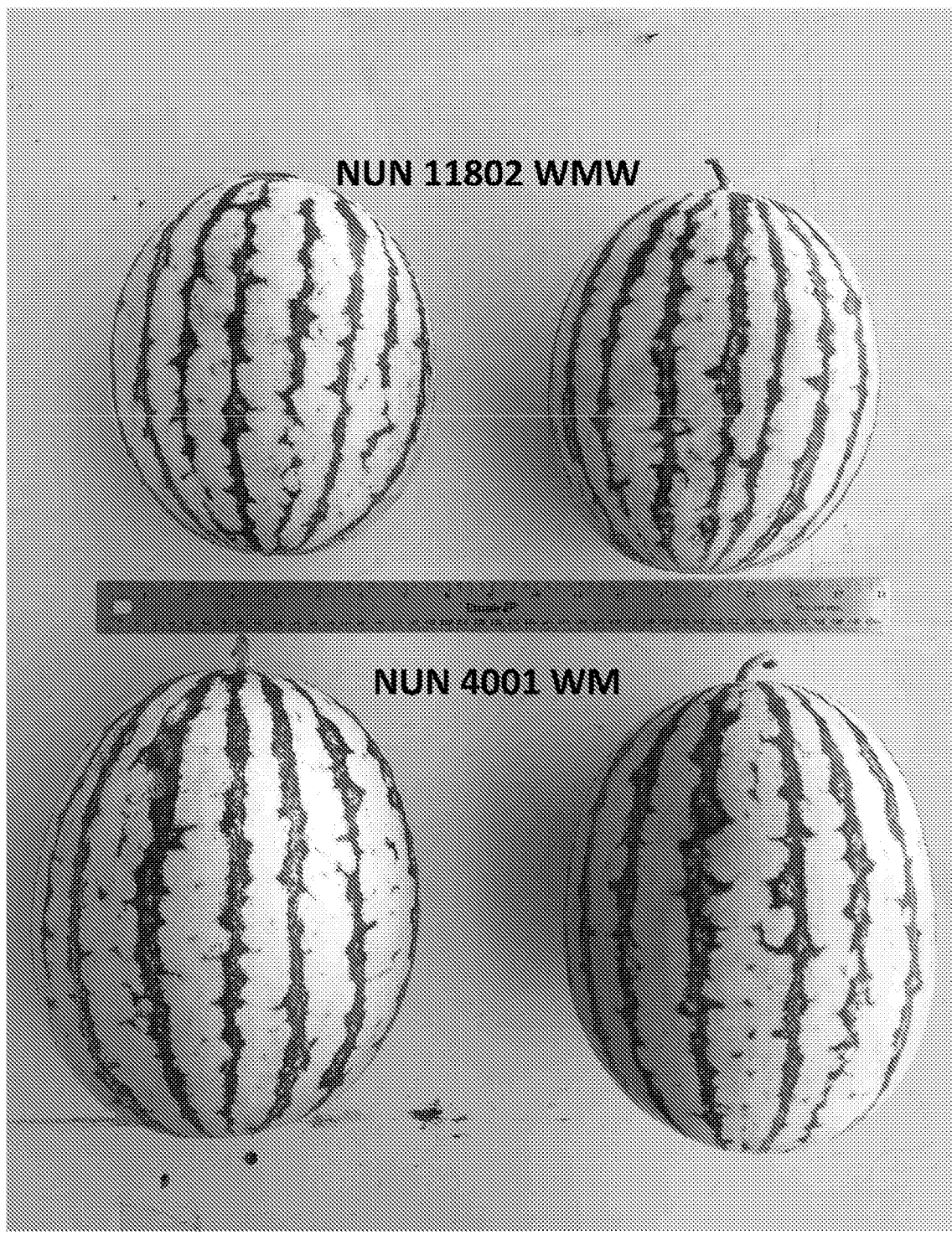
FIG. 2 shows the fruit comparison of watermelon variety NUN 11802 WMW and the Reference Variety.
Figure 3:
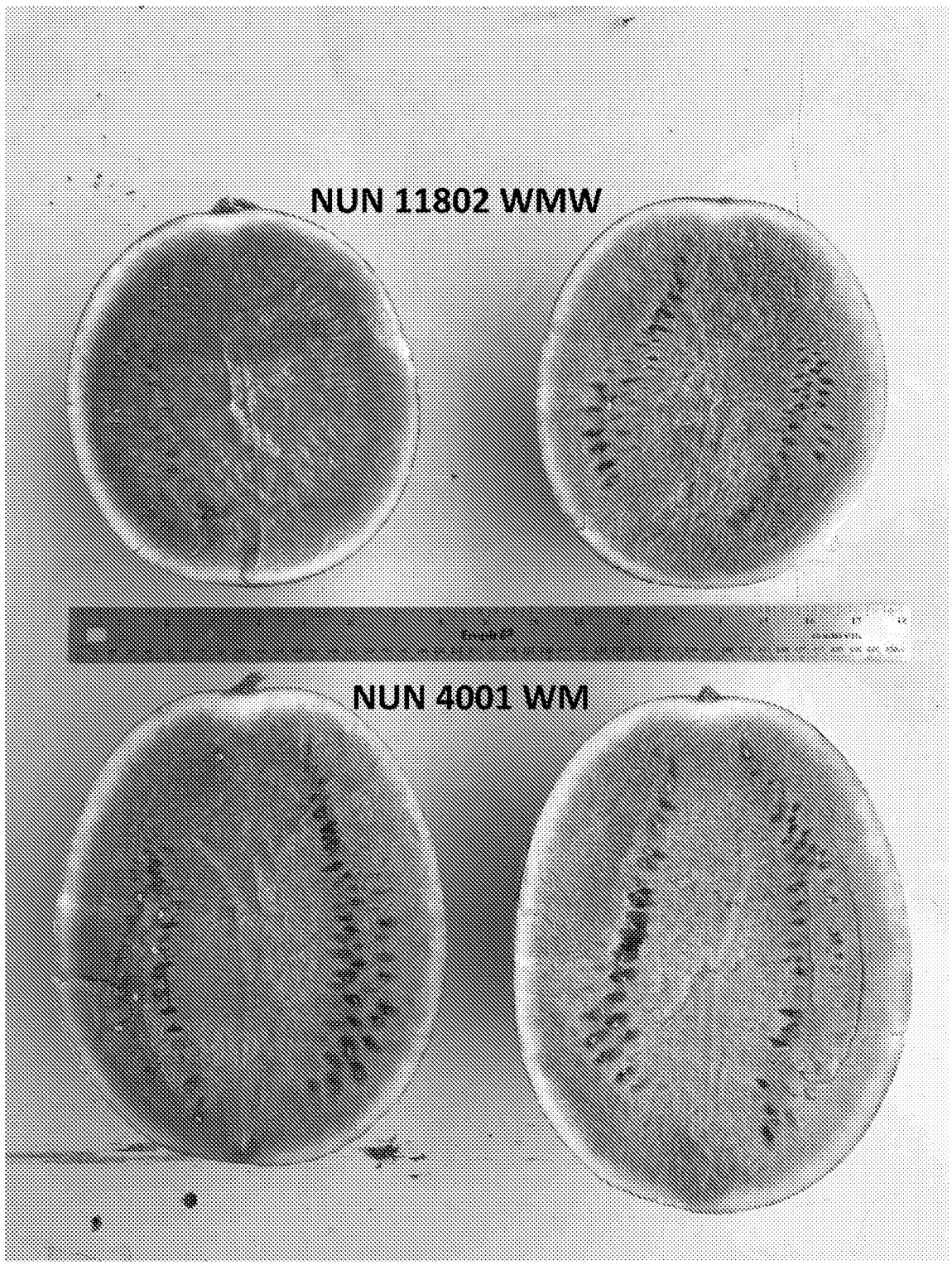
FIG. 3 shows the cross-section comparison of watermelon variety NUN 11802 WMW and the Reference Variety.
Figure 4:
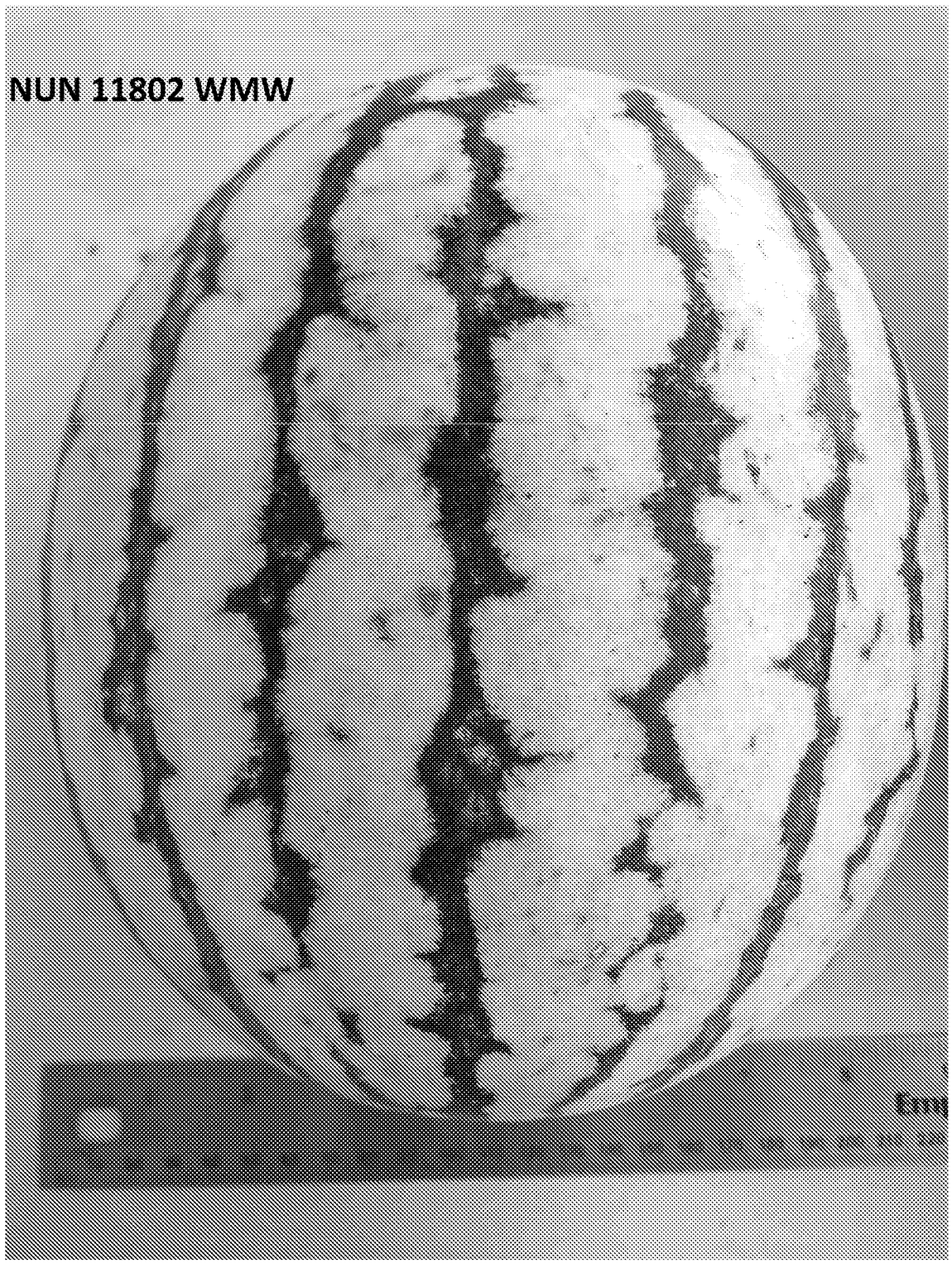
FIG. 4 shows the rind pattern of watermelon variety NUN 11802 WMW.
Figure 5:
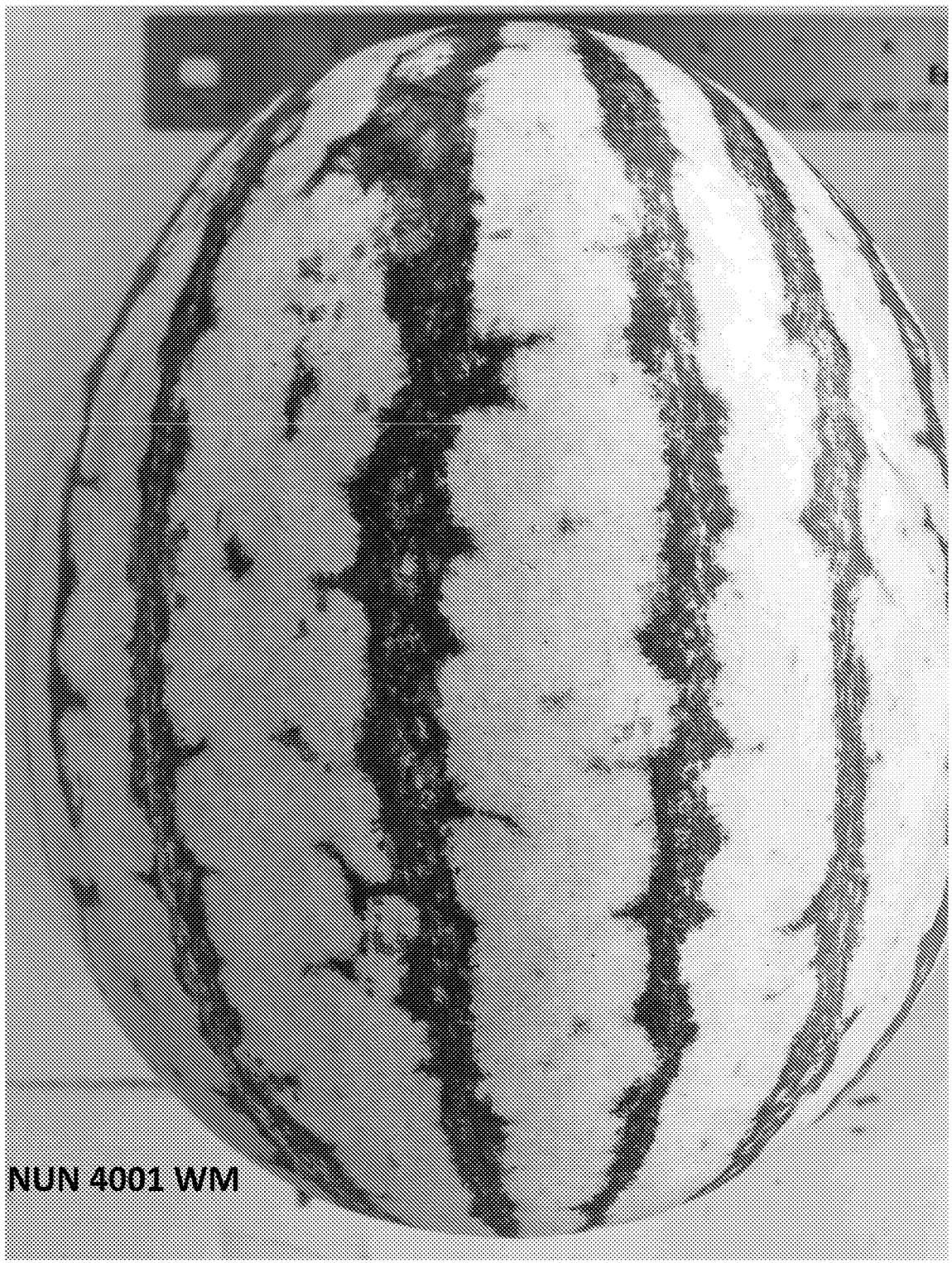
FIG. 5 shows the rind pattern of the Reference Variety.
Figure 6:
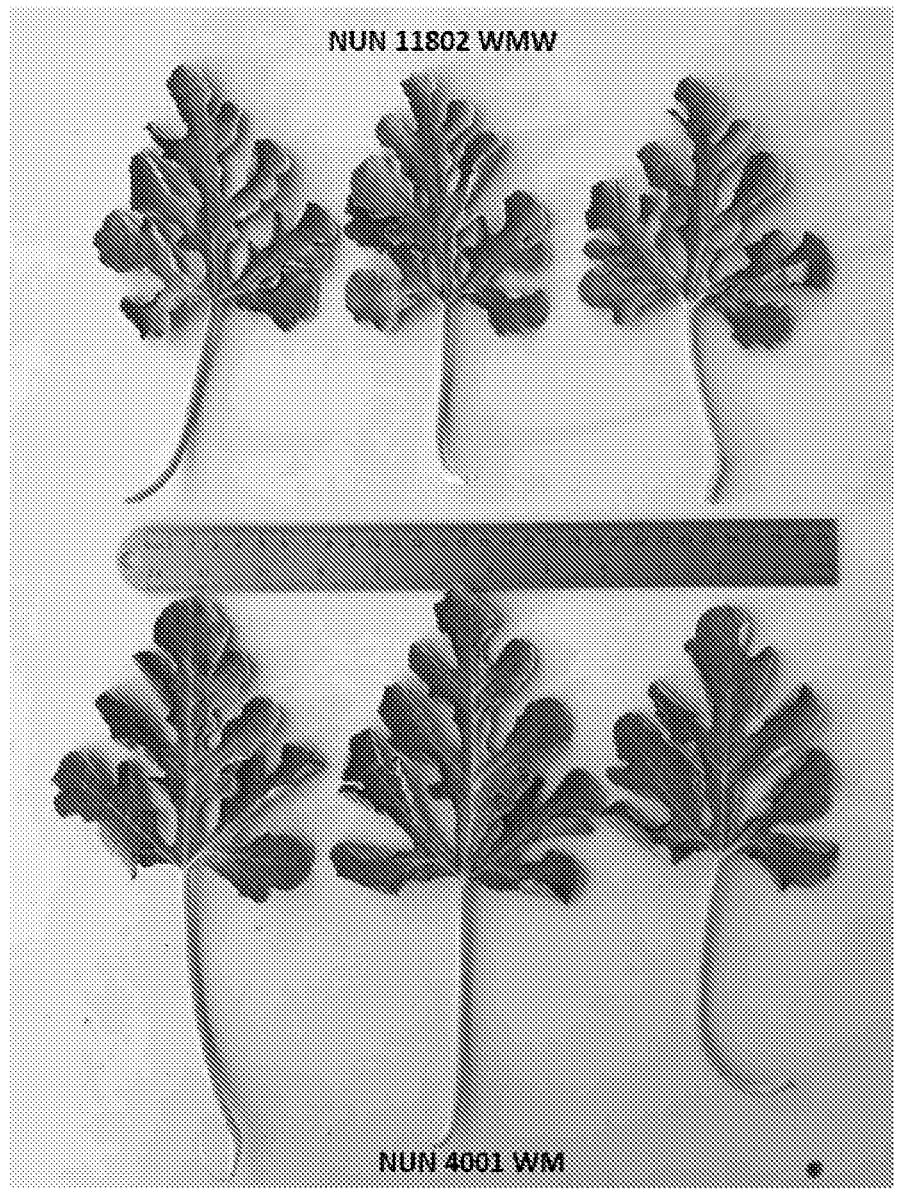
FIG. 6 shows the leaf comparison of watermelon variety NUN 11802 WMW and the Reference Variety.

"Watermelon" refers herein to plants of the species *Citrullus lanatus*. The most commonly eaten part of a watermelon is the fruit. The fruit comprises a stem and peduncle or pedicel, receptacle, ectocarp, rind, fruit flesh, exocarp, mesocarp, external phloem, internal phloem, xylem, vascular bundle, carpel, placenta and optionally seed. The stem and peduncle or pedicel, receptacle, ectocarp, rind, fruit flesh, exocarp, mesocarp, external phloem, internal phloem, xylem, vascular bundle, carpel, placenta and seedcoat of the seed are maternal tissues, and genetically identical to the plant on which they grow.

"Cultivated watermelon" refers to plants of *Citrullus lanatus* (e.g., varieties, breeding lines or cultivars of the species *C. lanatus*), cultivated by humans and having good agronomic characteristics.

The terms "watermelon plant designated NUN 11802 WMW," "NUN 11802 WMW," "NUN 11802," "NUN 11802 F1," "11802 WMW" or "watermelon 11802" are used interchangeably herein and refer to a watermelon plant of variety NUN 11802 WMW, representative seed of which has been deposited under Accession Number NCIMB 43701.

"Plant" includes the whole plant or any part or derivatives thereof, preferably having the same genetic makeup as the plant from which it is obtained.

"Plant part" includes any part of a plant, such as a plant organ (e.g., harvested or non-harvested fruits), a plant cell, a plant protoplast, a plant cell tissue culture or a tissue culture from which a whole plant can be regenerated, a plant cell that is intact in a plant, a clone, a micropropagation, plant callus, a plant cell clump, a plant transplant, a vegetative propagation, a seedling, a fruit, a harvested fruit, a part of a fruit, a leaf, a part of a leaf, pollen, an ovule, an embryo, a petiole, a shoot or a part thereof, a stem or a part thereof, a root or a part thereof, a root tip, a cutting, a seed, a part of a seed, a hypocotyl, a cotyledon, a scion, a graft, a stock, a rootstock, a pistil, an anther, or a flower or part thereof. Seed can be mature or immature. Pollen or ovules may be viable or non-viable. Also, any developmental stage is included, such as seedlings, cuttings prior or after rooting, mature plants or leaves. Alternatively, a plant part may also include a plant seed which comprises maternal tissues of watermelon variety NUN 11802 WMW and an embryo having one or two sets of chromosomes derived from the parent plant, e.g., from watermelon variety NUN 11802 WMW. Such an embryo comprises two sets of chromosomes derived from watermelon variety NUN 11802 WMW, if it is produced from self-pollination of watermelon variety NUN 11802 WMW, while an embryo derived from cross-fertilization of watermelon variety NUN 11802 WMW will comprise only one set of chromosomes from said variety.

A "seed of NUN 11802 WMW" refers to a watermelon seed which can be grown into a plant of variety NUN 11802 WMW, wherein a representative sample of viable seed of variety NUN 11802 WMW has been deposited under Accession Number NCIMB 43701. A seed can be in any stage of maturity, for example, a mature, viable seed, or an immature, non-viable seed. A seed comprises an embryo and maternal tissues.

An "embryo of NUN 11802 WMW" refers to an "F1 hybrid embryo" as present in a seed of watermelon variety NUN 11802 WMW, a representative sample of said seed of said watermelon variety has been deposited under Accession Number NCIMB 43701.

A "seed grown on NUN 11802 WMW" refers to a seed grown on a mature plant of variety NUN 11802 WMW or inside a fruit of watermelon variety NUN 11802 WMW. The "seed grown on NUN 11802 WMW" contains tissues and DNA of the maternal parent, watermelon variety NUN 11802 WMW.

A "fruit of NUN 11802 WMW" refers to a fruit containing maternal tissues of watermelon variety NUN 11802 WMW as deposited under Accession Number NCIMB 43701. In one option, the fruit contains seed grown on watermelon variety NUN 11802 WMW. In another option, the fruit does not contain seed, i.e., the fruit is parthenocarpic. The skilled person is familiar with methods for inducing parthenocarpy. Those methods comprise chemically or genetically inducing parthenocarpy, or by use of irradiated pollen (see, e.g., Moussa and Salem, 2010). Compounds suitable for chemically inducing parthenocarpy include auxins, gibberellins and cytokinins (see, e.g., Hayata et al., 1995). A fruit can be in any stage of maturity, for example, a mature fruit in the stage comprising viable seed, or an immature fruit comprising non-viable seed.

An "essentially homogeneous population of watermelon seed" is a population of seeds where at least 97%, 98%, 99% or more of the total population of seed are seed of watermelon variety NUN 11802 WMW.

An "essentially homogeneous population of watermelon plants" is a population of plants where at least 97%, 98%, 99% or more of the total population of plants are plants of variety NUN 11802 WMW.

The phrase "essentially free from other seed" refers to a population of seed where less than 3%, 2%, 1% or less of the total population of seed is seed that is not a watermelon seed or, in another aspect, less than 3%, 2%, 1% or less of the total population of seed is seed that is not seed of watermelon variety NUN 11802 WMW.

"Flavor" refers to the sensory impression of a food or other substance, especially a watermelon fruit or fruit part (fruit flesh) and is determined mainly by the chemical senses of taste and smell. Flavor is influenced by texture properties and by volatile and/or non-volatile chemical components (organic acids, lipids, carbohydrates, salts etc.)

"Aroma" refers to smell (or odor) characteristics of watermelon fruits or fruit parts (fruit flesh).

"Harvest maturity" is referred to as the stage at which a watermelon fruit is ripe or ready for harvest or the optimal time to harvest the fruit for the market, for processing or for consumption. In one aspect, harvest maturity is the stage which allows proper completion of the normal ripening.

"Harvested plant material" refers herein to plant parts (e.g., fruits detached from the whole plant), which have been collected for further storage and/or further use.

"Yield" means the total weight of all watermelon fruits harvested per hectare of a particular line or variety. It is understood that "yield" expressed as weight of all watermelon fruits harvested per hectare can be obtained by multiplying the number of plants per hectare times the "yield per plant."

"Marketable yield" means the total weight of all marketable watermelon fruits, especially fruit which is not cracked, damaged or diseased, harvested per hectare of a particular line or variety. A "marketable fruit" is a fruit that has commercial value.

"Hollow heart" is a disorder that varies among varieties. Hollow heart is marked by cracks in the heart of the watermelon fruit owing to accelerated growth in response to ideal growth conditions facilitated by ample water and arm temperatures.

"USDA descriptors" are the plant variety descriptors for Watermelon in the "Objective Description of Variety—Watermelon (*Citrullus lanatus*)," as published by the US Department of Agriculture, Agricultural Marketing Service, Plant Variety Protection Office, Beltsville, MD 20705 and which can be downloaded from the world-wide web at ams.usda.gov/sites/under services/plant-variety-protection/pvpo-c-forms under watermelon. "Non-USDA descriptors" are other descriptors suitable for describing watermelon.

"UPOV descriptors" are the plant variety descriptors described for watermelon in the "Guidelines for the Conduct of Tests for Distinctness, Uniformity and Stability, TG/142/5 (Geneva, 2013 and last revised 2019), as published by UPOV (International Union for the Protection of New Varieties and Plants), and which can be downloaded from the world-wide web at upov.int/edocs/tgdocs/en/tg142.pdf and is herein incorporated by reference in its entirety.

Likewise, "UPOV methods" to determine the specific parameters for the characterization of melon are described at upov.int.

"Calibration Manual: DUS Test for Watermelon (*Citrullus lanatus*)" refers to the calibration book for watermelon which provides guidance for describing a watermelon variety, as published by Naktuinbow (August 2017). The calibration manual was established by Naktuinbow in collaboration with the National Agriculture and Food Research Organization (NARO)/NCSS (Japan) and based on UPOV TG/142/5.

"RHS" or "RHS color chart" refers to the color chart of the Royal Horticultural Society (UK), which publishes a botanical color chart quantitatively identifying colors by a defined numbering system. The chart may be purchased from Royal Horticulture Society Enterprise Ltd. RHS Garden; Wisley, Woking; Surrey GU236QB, UK, e.g., the RHS color chart 2007.

"Reference Variety for NUN 11802 WMW" refers herein to watermelon variety NUN 4001 WM, a variety from Nunhems B.V., with the commercial name Premium, which has been planted in a trial together with watermelon variety NUN 11802 WMW. The characteristics of watermelon variety NUN 11802 WMW were compared to the characteristics of the Reference Variety as shown in Tables 2 and 3. The distinguishing characteristics between watermelon variety NUN 11802 WMW and the Reference Variety are shown in Table 4.

A plant having "all the physiological and morphological characteristics" of a referred-to-plant means a plant showing the physiological and morphological characteristics of the referred-to-plant when grown under the same environmental conditions, preferably in the same experiment; the referred-to-plant can be a plant from which it was derived, e.g., the progenitor plant, the parent, the recurrent parent, the plant used for tissue- or cell culture, etc. A physiological or morphological characteristic can be a numerical characteristic or a non-numerical characteristic. In one aspect, a plant has "all but one, two or three of the physiological and morphological characteristics" of a referred-to-plant, or "all the physiological and morphological characteristics" of Tables 1-3 or "all or all but one, two or three of the physiological and morphological characteristics" of Tables 1-3.

The physiological and/or morphological characteristics mentioned above are commonly evaluated at significance levels of 1%, 5% or 10% if they are numerical (quantitative), or for having an identical degree (or type) if not numerical (not quantitative), if measured under the same environmental conditions. For example, a progeny plant or a Single Locus Converted plant or a mutated plant of variety NUN 11802 WMW may have one or more (or all) of the essential physiological and/or morphological characteristics of said variety listed in Tables 1-3, as determined at the 5% significance level (i.e., $p<0.05$), when grown under the same environmental conditions.

"Distinguishing characteristics" or "distinguishing morphological and/or physiological characteristics" refers herein to the characteristics which distinguish the new variety from other watermelon varieties, such as the Reference Variety (e.g., are different), when grown under the same environmental conditions. The distinguishing characteristics between watermelon variety NUN 11802 WMW and Reference Variety are described herein and also can be seen in Table 4. When comparing watermelon variety NUN 11802 WMW to other varieties, the distinguishing characteristics may be different. In one aspect, the distinguishing characteristics may include one, two, three or more (or all) of the characteristics listed in Tables 1-3. All numerical distinguishing characteristics are statistically significantly different at p<0.05 between NUN 11802 WMW and the other variety, (e.g. the Reference Variety).

Watermelon variety NUN 11802 WMW has the following distinguishing characteristics when compared to the Reference Variety as shown in Table 4: 1) round small fruit type; 2) larger stem diameter; 3) shorter leaf length; 4) narrower leaf width; 5) grey green leaf color; 6) shorter petiole length; 7) smaller petiole width; 8) shorter fruit length; 9) smaller fruit diameter; 10) lighter fruit weight; 11) lighter yellow green primary color (ground color); 12) dark grey green secondary color (stripes); 13) broad elliptic fruit shape in longitudinal section; 14) weaker conspicuousness of veining; 15) one colored and marbled pattern of stripes; 16) shorter peduncle length; 17) smaller peduncle width; 18) smaller stem end thickness; 19) lower % soluble solids, when determined at 5% significance level for numerical characteristics and determined by type or degree for non-numerical characteristics for plants grown under the same environmental conditions Thus, a watermelon plant "comprising the distinguishing characteristics of variety NUN 11802 WMW" (such as a progeny plant) refers herein to a plant which does not differ significantly from said variety in the distinguishing characteristics above. Therefore, in one aspect a plant is provided which does not differ significantly from watermelon variety NUN 11802 WMW in the distinguishing characteristics above.

Similarity and differences between two different plant lines or varieties can be determined by comparing the number of morphological and/or physiological characteristics that are the same (i.e., statistically not significantly different) or that are different (i.e., statistically significantly different) between the two plant lines or varieties using plants grown under the same environmental conditions. A numerical characteristic is considered to be "the same" when the value for a numeric characteristic is not significantly different at the 1% (p<0.01) or 5% (p<0.05) significance level, using T-test, a standard method known to the skilled person. A non-numerical or "degree" or "type" characteristic is considered "the same" when the values have the same "degree" or "type" when scored using USDA and/or UPOV descriptors, if the plants are grown under the same environmental conditions.

In one aspect, a statistical analysis of the quantitative characteristics showing the degree of significance may be provided. Statistical significance is the likelihood that a relationship between two or more variables is caused by something other than chance, i.e., that the differences in the means for quantitative characteristics of the plant of watermelon variety NUN 11802 WMW and the Reference Variety are significant due to chance. For the purpose of proving differences or distinction between watermelon variety NUN 11802 WMW and the Reference Variety, a p-value of 5% or 0.05 or lower is considered statistically significant. This means that there is only a 5% probability that the observed result could have happened just by chance or random variation.

The statistical analysis is drawn from a small sample of at least 15 plants or plant parts of watermelon variety NUN 11802 WMW and the Reference Variety. Statistical points or parameters such as mean, minimum, median, maximum, and standard deviation are collected from the sample data to analyze where the average is, how varied the data set is, and whether the data is skewed. For the purpose of determining whether the result of the data set is statistically significant, a T-Test is used, a statistical tool for proving significance in the means of the two groups (e.g., watermelon variety NUN 11802 WMW and the Reference Variety) at 5% significance level (a p-value of 5% or 0.05).

"Variety" or "cultivar" means a plant grouping within a single botanical taxon of the lowest rank.

A "plant line" is, for example, a breeding line which can be used to develop one or more varieties. A breeding line is typically highly homozygous.

"Harvested seeds" refer to seeds harvested from a line or variety, e.g., produced after self-fertilization or cross-fertilization and collected.

"Hybrid variety" or "F1 hybrid" refers to the seeds harvested from crossing two inbred (nearly homozygous) parental lines. For example, the female parent is pollinated with pollen of the male parent to produce hybrid (F1) seeds on the female parent.

"Locus" (plural loci) refers to the specific location, place or site of a DNA sequence on a chromosome, where, for example, a gene or genetic marker is found. A locus may confer a specific trait.

"Allele" refers to one or more alternative forms of a gene locus. All of these loci relate to one trait. Sometimes, different alleles can result in different observable phenotypic traits, such as different pigmentation. However, many variations at the genetic level result in little or no observable variation. If a multicellular organism has two sets of chromosomes, i.e., diploid, these chromosomes are referred to as homologous chromosomes, i.e., diploid. Diploid organisms have one copy of each gene (and therefore one allele) on each chromosome. If both alleles are the same, they are homozygotes. If the alleles are different, they are heterozygotes.

"Genotype" refers to the genetic composition of a cell or organism.

"Phenotype" refers to the detectable characteristic of a plant, cell, or organism, which characteristics are the manifestation of gene expression.

"Haploid" refers to a cell or organism having one set of the two sets of chromosomes in a diploid.

"Diploid" refers to a plant, a vegetative plant part(s), or seed which a diploid plant can be grown, having two sets of chromosomes, designated herein as 2n.

"Triploid" refers to a plant, a vegetative plant part(s), or seed which a diploid plant can be grown, having three sets of chromosomes, designated herein as 3n.

"Tetraploid" refers to a plant, a vegetative plant part(s), or seed which a diploid plant can be grown, having four sets of chromosomes, designated herein as 4n.

"Polyploid" refers to a plant, a vegetative plant part(s), or seed which a diploid plant can be grown, having three or more complete sets of chromosomes.

"Pollenizer plant" or "pollinizer" refers to the (inbred or hybrid) diploid plant, or parts thereof (e.g., its pollen or scion), suitable as pollinizer for inducing fruit set on triploid plants. A pollinizer plant is, thus, able to lead to good fruit set (and good triploid fruit yield) of triploid plants, by producing an appropriate amount of pollen at the appropriate day-time and for an appropriate period of time.

"Female parent" or "tetraploid parent" refers to the plant which is pollinated with pollen of male parent, leading to the production of fruits containing triploid seeds. The female parent is optionally is inbred so that it is nearly homozygous and stable.

"Male parent" refers to the pollinizer plant used as male parent for inducing fruit set and seed production on a tetraploid female parent, resulting in F1 hybrid triploid seeds. Optionally, one or both the male parent and the female parent are inbred. If both male and female parent are inbred, i.e., each parent is nearly homozygous and stable, the resulting hybrid triploid will also be genetically uniform and stable.

"Hybrid triploid plant" or "F1 triploid plant" is a triploid plant grown from hybrid, triploid seed obtained from cross fertilizing a male diploid parent with a female tetraploid parent.

"Seedless fruit" are triploid fruit which contain no mature seeds. The fruit may contain one or more small, edible, white ovules.

"Scion" refers to a part of the plant attached to the rootstock. This plant is selected for its stems, leaves, flowers, or fruits. The scion contains the desired genes to be duplicated in future production by the stock/scion plant and may produce the desired watermelon fruit.

"Rootstock" or "stock" refers to the plant selected for its root system, in particular for the resistance of the roots to diseases or stress (e.g., heat, cold, salinity etc.) Generally, the quality of the fruit of the plant providing the rootstock is less important. It is noted that during the grafting process, the rootstock root system may be removed, which later grows back to develop a functional root system of the grafted seedling. Thus, when referring to the rootstock during the grafting method, this rootstock may be with or without the root system. When referring to the rootstock of the grafted seedlings or plants, the re-grown root system is encompassed.

"Stock/scion" or "grafted plant" refers to a watermelon plant comprising a rootstock from one plant grafted to a scion from another plant.

"Grafting" refers to the method of joining of (genetically) different plant parts, especially scions and rootstocks, together so that they grow as a single plant. A grafted seedling or a grafted plant is a seedling or plant (produced by grafting) consisting of such different plant parts and which grows as one plant.

A "non-grafted" watermelon seedling or plant refers to a seedling or plant grown from a seed (without grafting).

A "single grafted" watermelon seedling or "single grafted" watermelon plant refers to a grafted seedling or plant consisting of a single watermelon scion (e.g., triploid watermelon scion or a diploid watermelon scion) joined with a genetically different rootstock such as a gourd or squash rootstock, another watermelon rootstock, or a transgenic rootstock, etc.

A "double grafted" watermelon seedling or a "double grafted" watermelon plant is herein grafted seedling or plant comprising two watermelon scions grafted onto a single rootstock. In one aspect, two genetically different watermelon scions, namely a triploid watermelon scion and a diploid watermelon scion, are grafted onto a genetically different rootstock, such as a gourd or squash rootstock, another watermelon rootstock, or a transgenic rootstock, etc. in another aspect, two triploid watermelon scions, or two diploid watermelon scions, are grafted onto a genetically different rootstock, such as a gourd or squash rootstock, another watermelon rootstock, or a transgenic rootstock, etc.

A "transplant" or 'seedling transplant' refers to a watermelon seedling which is at a developmental stage and condition so that it can be transplanted into the field or greenhouse for growth, fruit production and harvest. The word transplant or seedling transplant can thus, encompass single-grafted, double-grafted, or non-grafted seedlings.

"Interplanting" refers to the combination of two or more type of seeds and/or transplants sown or planted (or transplanted) on the same field, especially the sowing and/or planting (or transplanting) of pollenizers in the same field as triploid hybrid plants (for seedless fruit production on the triploid plants and diploid fruit production on the pollinizer plants). For example, the pollinizer may either be planted in separate rows or interplanted with the triploid plants in the same row (e.g., in hills within each row). Pollenizers may also be planted in between rows of triploids. Also, seeds of pollenizers and triploid hybrids may be mixed prior to seedling, resulting in random seeding. The transplants of the triploid hybrid plants and/or pollinizer plants may also comprise a rootstock of a different plant. Suitable rootstocks are known in the art. Watermelon plants with a different rootstock are referred to as "grafted."

"Planting" or "planted" refers to seeding (direct sowing) or transplanting seedlings (plantlets) into a field by machine or hand.

The term "traditional breeding techniques" encompasses herein crossing, selfing, selection, doubled haploid production, embryo rescue, protoplast fusion, marker assisted selection, mutation breeding etc. as known to the breeder (i.e., methods other than genetic modification/transformation/transgenic methods), by which, for example, a genetically heritable trait can be transferred from one watermelon line or variety to another.

"Tissue culture" or "cell culture" refers to a composition comprising isolated cells of the same or a different type or a collection of such cells organized into parts of a plant. Tissue culture of various tissues of watermelon and regeneration of plants therefrom is well known and widely published (see, e.g., Compton et al., *Plant Cell, Tissue and Organ Culture* 77: 231-243, 2004). Similarly, methods for preparing a "tissue culture" or "cell culture" are well known in the art.

"Regeneration" refers to the development of a plant from cell culture or tissue culture or vegetative propagation.

"Vegetative propagation," "vegetative reproduction," or "clonal propagation" are used interchangeably herein and mean a method of taking a plant part and inducing or allowing that plant part to form at least roots, and also refer to the plant or plantlet obtained by that method. Optionally, the vegetative propagation is grown into a mature plant. The skilled person is aware of what plant parts are suitable for use in the method.

"Crossing" refers to the mating of two parent plants. The term encompasses "cross-pollination" and "selfing".

"Selfing" refers to self-pollination of a plant, i.e., the transfer of pollen from the anther to the stigma of the same plant.

"Cross-pollination" refers to the fertilization by the union of two gametes from different plants.

"Backcrossing" is a traditional breeding technique used to introduce a trait into a plant line or variety. The plant containing the trait is called the donor plant and the plant into which the trait is transferred is called the recurrent parent. An initial cross is made between the donor parent and the recurrent parent to produce a progeny plant. Progeny plants which have the trait are then crossed to the recurrent parent. After several generations of backcrossing and/or selfing the recurrent parent comprises the trait of the donor. The plant generated in this way may be referred to as a "single trait converted plant". The technique can also be used on a parental line of a hybrid.

"Progeny" as used herein refers to a plant obtained from a plant designated NUN 11802 WMW. A progeny may be obtained by regeneration of cell culture or tissue culture or parts of a plant of said variety or selfing of a plant of said variety or by producing seeds of a plant of said variety. In further aspects, progeny may also encompass plants obtained from crossing of at least one plant of said variety with another watermelon plant of the same variety or another variety or line, or with wild watermelon plants. A progeny may comprise a mutation or a transgene. A "first generation progeny" is the progeny directly derived from, obtained from, or derivable from the parent plant by, e.g., traditional breeding methods (selfing and/or cross-pollinating) or regeneration (optionally combined with transformation or mutation). Thus, a plant of variety NUN 11802 WMW is the male parent, the female parent or both of a first generation progeny of watermelon variety NUN 11802 WMW. Progeny may have all the physiological and morphological characteristics of variety NUN 11802 WMW, when grown under the same environmental conditions. Using methods such as backcrossing, recurrent selection, mutation or transformation, one or more specific characteristics may be introduced into said variety, to provide or a plant comprising all but 1, 2, or 3 of the morphological and physiological characteristics of variety NUN 11802 WMW.

The terms "gene converted" or "conversion plant" or "single locus converted plant" in this context refer to watermelon plants which are developed by traditional breeding techniques, e.g., backcrossing or via genetic engineering or through mutation breeding, wherein essentially all of the desired morphological and physiological characteristics of the parent variety or line are recovered, in addition to the one or more characteristics introduced into the parent via e.g., the backcrossing technique (optionally including reverse breeding or reverse synthesis of breeding lines). It is understood that not only the addition of a further characteristic (e.g., addition of gene conferring a further characteristic, such as a disease resistance gene), but also the replacement/modification of an existing characteristic by a different characteristic is encompassed herein (e.g., mutant allele of a gene can modify the phenotype of a characteristic).

Likewise, a "Single Locus Converted (Conversion) Plant" refers to plants developed by plant breeding techniques comprising or consisting of mutation and/or by genetic transformation and/or by traditional breeding techniques, such as backcrossing, wherein essentially all of the desired morphological and physiological characteristics of a watermelon variety are recovered in addition to the characteristics of the single locus having been transferred into the variety via the abovementioned technique, or wherein the morphological and physiological characteristics of the variety has been replaced/modified in the variety. In case of a hybrid, the gene may be introduced in the male or female parental line.

"Transgene" or "chimeric gene" refers to a genetic locus comprising a DNA sequence which has been introduced into the genome of the plant by transformation. A plant comprising a transgene stably integrated into its genome is referred to as "transgenic plant."

As used herein, the terms "resistance" and "tolerance" are used interchangeably to describe plants that show no symptoms or significantly reduced symptoms to a specified biotic pest, pathogen, abiotic influence or environmental condition compared to a susceptible plant. These terms are optionally also used to describe plants showing some symptoms but that are still able to produce marketable product with an acceptable yield.

"Average" refers herein to the arithmetic mean.

The term "mean" refers to the arithmetic mean of several measurements. The skilled person understands that the appearance of a plant depends to some extent on the growing conditions of said plant. The mean, if not indicated otherwise within this application, refers to the arithmetic mean of measurements on at least 15 different, randomly selected plants of a variety or line.

DETAILED DESCRIPTION OF THE VARIOUS ASPECTS OF THE DISCLOSURE

The disclosure relates to a plant of variety NUN 11802 WMW, wherein a representative sample of seeds of said variety has been deposited under the Budapest Treaty, with Accession number NCIMB 43701. NUN 11802 WMW is a round oval, diploid watermelon variety of the mini-seeded type and is suitable for growing in the open field.

In another aspect, watermelon variety NUN 11802 WMW, or a part thereof, or a progeny thereof, comprises intermediate resistance to *Fusarium oxysporum* f. s.p *niveum* Race 0 and Race 1, measured according to UPOV standards described in TG142/5.

The disclosure also provides for a watermelon plant or part thereof having all of the physiological and morphological characteristics of the plant of watermelon variety NUN 11802 WMW when grown under the same environmental conditions.

The disclosure further relates to a watermelon variety NUN 11802 WMW, which when compared to its Reference Variety has the following distinguishing characteristics as shown in Table 4: 1) round small fruit type; 2) larger stem diameter; 3) shorter leaf length; 4) narrower leaf width; 5) grey green leaf color; 6) shorter petiole length; 7) smaller petiole width; 8) shorter fruit length; 9) smaller fruit diameter; 10) lighter fruit weight; 11) lighter yellow green primary color (ground color); 12) dark grey green secondary color (stripes); 13) broad elliptic fruit shape in longitudinal section; 14) weaker conspicuousness of veining; 15) one colored and marbled pattern of stripes; 16) shorter peduncle length; 17) smaller peduncle width; 18) smaller stem end thickness; 19) lower % soluble solids, when determined at 5% significance level for numerical characteristics and determined by type or degree for non-numerical characteristics for plants grown under the same environmental conditions. Also encompassed are parts of that plant.

In one aspect, the plant of variety NUN 11802 WMW or a progeny plant thereof, comprises all of the following morphological and/or physiological characteristics (i.e., average values of numerical characteristics, as indicated on the USDA Objective description of variety—watermelon (unless indicated otherwise)) as shown in Tables 1-3, where the numerical characteristics are determined at the 5% significance level for plants and determined by type or degree for non-numerical characteristics for plants grown under the same environmental conditions. A part of this plant is also provided.

The disclosure further provides a watermelon plant which does not differ from the physiological and morphological characteristics of the plant of variety NUN 11802 WMW as determined at the 1%, 2%, 3%, 4%, or 5% significance level when grown under the same environmental conditions. In a particular aspect, the plants are measured in the same trial (e.g., the trial is conducted as recommended by the USDA or UPOV). The disclosure also comprises a part of said plant, preferably a fruit or part thereof.

The morphological and/or physiological differences between two different individual plants described herein (e.g., between watermelon variety NUN 11802 WMW and a progeny thereof) or between a plant of variety NUN 11802

WMW or progeny of said variety, or a plant having all, or all but 1, 2, or 3, of the physiological and morphological characteristics of variety NUN 11802 WMW (or all, or all but 1, 2, or 3 of the characteristics as listed in Tables 1-3) and another known variety can easily be established by growing said variety next to each other (in the same field, under the same environmental conditions), preferably in several locations which are suitable for said watermelon cultivation, and measuring the morphological and physiological characteristics of a representative number of plants (e.g., to calculate an average value and to determine the variation range/uniformity within the variety). For example, trials can be carried out in Acampo CA, USA (N 38 degrees 07'261"/W 121 degrees 18' 807", USA), whereby various characteristics, for example, fruit type, maturity category, ploidy, plant sex form, leaf shape, leaf color, lobing, flower color, fruit shape, average fruit weight, fruit color, stripes, rind texture, flesh texture, flesh color, % soluble solids of juice, penetrometer resistance reading, disease resistance, and insect resistance can be measured and directly compared for species of watermelon.

Also, at-harvest and/or post-harvest characteristics of fruits can be compared, such as cold storage holding quality, post-harvest flesh firmness, and Brix can be measured using known methods. (Fruit) Flesh firmness can, for example, be measured using a penetrometer, e.g. by inserting a probe into the fruit flesh and determining the insertion force, or by other methods. Fruit flesh firmness can for example be measured using a "FT 327 Penetrometer", available from QA Supplies LLC, 1185 Pineridge Road, Norfolk, VA 23502.

Thus, the disclosure comprises watermelon plant having one, two or three physiological and/or morphological characteristics which are different from those of the plant of variety NUN 11802 WMW and which otherwise has all the physiological and morphological characteristics of the plant of variety NUN 11802 WMW, when determined (e.g., at the 5% significance level for quantitative characteristics or determined by type for non-quantitative characteristics) for plants grown under the same environmental conditions. In one aspect, the different characteristic(s) is/are a result of breeding with watermelon variety NUN 11802 WMW and selection of a progeny plant comprising one, two, or three characteristics which are different than in watermelon variety NUN 11802 WMW. In another aspect, the different characteristic is the result of a mutation (e.g., spontaneous mutation of a human induced mutation through, e.g., targeted mutagenesis or traditional mutagenesis such as chemically or radiation induced mutagenesis) or it is a result of transformation.

The disclosure also relates to a seed of watermelon variety NUN 11802 WMW, wherein a representative sample of said seed has been deposited under the Budapest Treaty, with Accession number NCIMB 43701.

In another aspect, a seed of hybrid variety NUN 11802 WMW is obtainable by crossing the male parent of watermelon variety NUN 11802 WMW with the female parent of watermelon variety NUN 11802 WMW and harvesting the seeds produced on the female parent. The resultant seeds of said variety can be grown to produce plants of said variety.

In another aspect, the disclosure provides a plant grown from a seed of watermelon variety NUN 11802 WMW and plant part thereof.

The disclosure also provides a watermelon fruit produced on a plant grown from a seed of watermelon variety NUN 11802 WMW.

In another aspect, the disclosure provides for a watermelon plant part of variety NUN 11802 WMW, preferably a fruit or part thereof, a representative sample of seed from said variety has been deposited under the Budapest Treaty, with Accession number NCIMB 43701.

Also provided is a plant of variety NUN 11802 WMW, or a fruit or other plant part thereof, produced from a seed, wherein a representative sample of said seeds has been deposited under the Budapest Treaty, with Accession Number NCIMB 43701.

Also provided is a plant part obtained from variety NUN 11802 WMW, wherein said plant part is a fruit, a harvested fruit, a part of a fruit, a leaf, a part of a leaf, pollen, an ovule, a cell, a petiole, a shoot or a part thereof, a stem or a part thereof, a root or a part thereof, a root tip, a cutting, a seed, a part of a seed, seed coat or another maternal tissue which is part of a seed grown on said variety, a hypocotyl, a cotyledon, a scion, a stock, a rootstock, a pistil, an anther, and a flower or a part thereof. Such plant parts may be suitable for sexual reproduction (e.g., a pollen, a flower, an ovary, an ovule, an embryo, etc.), vegetative reproduction (e.g., a cutting, a root, a stem, a cell, a protoplast, a leaf, a cotyledon, a meristem, etc.) or tissue culture (e.g., a leaf, a pollen, an embryo, a cotyledon, a hypocotyl, a cell, a root, a root tip, an anther, a flower, a seed, a stem, etc.) Fruits are particularly important plant parts. Fruits may be parthenocarpic, or seedless, or contain immature or nonviable seeds, or contain viable seeds.

In a further aspect, the plant part obtained from variety NUN 11802 WMW is a cell, optionally a cell in a cell or tissue culture. That cell may be grown into a plant of variety NUN 11802 WMW. A part of variety NUN 11802 WMW (or of a progeny of that variety or of a plant having all physiological and/or morphological characteristics but one, two or three of watermelon variety NUN 11802 WMW) further encompasses any cells, tissues, organs obtainable from the seedlings or plants in any stage of maturity.

The disclosure also provides a tissue or cell culture comprising cells of watermelon variety NUN 11802 WMW. Such a tissue culture can, for example, be grown on plates or in liquid culture, or be frozen for long term storage. The cells of watermelon variety NUN 11802 WMW used to start the culture can be selected from any plant part suitable for vegetative reproduction, or in a particular aspect can be cells of an embryo, a meristem, a cotyledon, a hypocotyl, pollen, a leaf, an anther, a root, a root tip, a pistil, a petiole, a flower, a fruit, a seed, or a stem. In another particular aspect, the tissue culture does not contain somaclonal variation or has reduced somaclonal variation. The skilled person is familiar with methods to reduce or prevent somaclonal variation, including regular re-initiation.

In one aspect, the disclosure provides a watermelon plant regenerated from the tissue or cell culture of watermelon variety NUN 11802 WMW, wherein the regenerated plant is not significantly different from watermelon variety NUN 11802 WMW in all, or all but one, two, or three, of the physiological and morphological characteristics, e.g., determined at the 5% significance level for numerical characteristics and determined by type or degree for non-numerical characteristics when grown under the same environmental conditions. Optionally, the plant has one, two, or three the physiological and morphological characteristics that are affected by a mutation or by transformation. In another aspect, the disclosure provides a watermelon plant regenerated from the tissue or cell culture of variety NUN 11802 WMW, wherein the plant has all of the physiological and morphological characteristics of said variety, e.g., determined at the 5% significance level for numerical characteristics and determined by type or degree for non-numerical characteristics when grown under the same environmental conditions. Similarity or difference of a characteristic is determined by measuring that characteristics on a representative number of plants grown under the same environmental conditions, determining whether type/degree characteristics are the same and determining whether numerical characteristics are different at the 5% significance level.

Watermelon variety NUN 11802 WMW, or its progeny, or a plant having all physiological and/or morphological characteristics but one, two or three which are different from those of variety NUN 11802 WMW, can also be reproduced using vegetative reproduction methods. Therefore, the disclosure provides for a method of producing a plant, or a plant part, of variety NUN 11802 WMW, comprising vegetative propagation of said variety. Vegetative propagation comprises regenerating a whole plant from a plant part of variety NUN 11802 WMW or from a progeny or from or a plant having all physiological and/or morphological characteristics of said variety but one, two or three different characteristics, such as a cutting, a cell culture, or a tissue culture.

The disclosure also provides methods of vegetatively propagating a part of the plant of variety NUN 11802 WMW. In certain aspects, the method comprises: (a) cultivating tissue or cells capable of being propagated from NUN 11802 WMW to obtain proliferated shoots; and (b) rooting said proliferated shoots, to obtain rooted plantlets. Steps (a) and (b) may also be reversed, i.e., first cultivating said tissue to obtain roots and then cultivating the tissue to obtain shoots, thereby obtaining rooted plantlets. The rooted plantlets may then be further grown, to obtain plants. In one embodiment, the method further comprises step (c) growing plants from said rooted plantlets. Therefore, the method also comprises regenerating a whole plant from a part of variety NUN 11802 WMW. In a particular aspect, the part of the plant to be propagated is a cutting, a cell culture or a tissue culture.

The disclosure also provides for a vegetatively propagated plant of variety NUN 11802 WMW (or from progeny of variety NUN 11802 WMW or from or a plant having all but one, two or three physiological and/or morphological characteristics of variety NUN 11802 WMW), wherein the plant has all of the morphological and physiological characteristics of variety NUN 11802 WMW when the characteristics are determined at the 5% significance level for plants grown under the same conditions. In another aspect, the propagated plant has all but one, two or three of the morphological and physiological characteristics of variety NUN 11802 WMW when the characteristics are determined at the 5% significance level for plants grown under the same conditions. A part of said propagated plant or said propagated plant with one, two or three differences is also provided. In another aspect, the propagated plant has all or all but 1, 2, or 3 of the physiological and morphological characteristics of watermelon variety NUN 11802 WMW (e.g., as listed in Tables 1-3).

In another aspect, the disclosure provides a method for producing a watermelon plant part, preferably a fruit, comprising growing a plant of variety NUN 11802 WMW until it sets at least one fruit, and collecting the fruit. Preferably, the fruit is collected at harvest maturity. In another aspect, the fruit is collected when the seed is ripe. In a particular aspect, all fruits on a truss can be harvested together. In another particular aspect, all fruit on a watermelon plant can be harvested at the same time.

In another aspect, the plant of variety NUN 11802 WMW can be produced by seeding directly in the soil (e.g., the field) or by germinating the seeds in a controlled environment (e.g., greenhouse) and optionally then transplanting the seedlings into the field (see, e.g., Baameur, et. Al., University of California, Division of Agriculture and Natural Resources, Publication 7213, 2009, 1-5). Watermelon can also be grown entirely in greenhouses. For example, a seed is sown into a prepared seed bed in a field where the plant remains for its entire life. Alternatively, the seed may be planted through a black plastic mulch. The dark plastic will absorb heat from the sun, warming the soil early. It will also help to conserve moisture during the growing season, controls weed and makes harvesting easier and cleaner. Triploid varieties should be interplanted with pollenizers to set fruit.

In another aspect, the plant and plant parts of watermelon variety NUN 11802 WMW and progeny of said variety are provided, e.g., grown from seeds, produced by sexual or vegetative reproduction, regenerated from the above-described plant parts, or regenerated from cell or tissue culture of the watermelon variety NUN 11802 WMW, in which the reproduced (seed propagated or vegetatively propagated) plant has all of the physiological and morphological characteristics of watermelon variety NUN 11802 WMW, e.g., listed in Tables 1-3. In one aspect, said progeny of watermelon variety NUN 11802 WMW can be modified in one, two, or three characteristics, in which the modification is a result of mutagenesis or transformation with a transgene.

In another aspect, the disclosure provides a progeny plant of variety NUN 11802 WMW such as a progeny plant obtained by further breeding of variety NUN 11802 WMW. Further breeding with variety NUN 11802 WMW includes selfing that variety and/or cross-pollinating variety NUN 11802 WMW with another watermelon plant one or more times. In particular, the disclosure provides for a progeny plant that retains all the morphological and physiological characteristics of variety NUN 11802 WMW or, in another aspect, a progeny plant that retains all, or all but one, two, or three, of the morphological and physiological characteristics of variety NUN 11802 WMW, optionally all or all but one, two, or three of the characteristics as listed in Tables 1-3, e.g., determined at the 5% significance level for numerical characteristics and determined by type or degree for non-numerical characteristics, when grown under the same environmental conditions. In another aspect, the progeny is a first generation progeny, i.e., the ovule or the pollen (or both) used in the crossing is an ovule or pollen of watermelon variety NUN 11802 WMW, where the pollen comes from an anther of watermelon variety NUN 11802 WMW and the ovule comes from an ovary of watermelon variety NUN 11802 WMW. In another aspect, the disclosure provides for a vegetative reproduction of watermelon variety NUN 11802 WMW and a plant having all, or all but 1, 2, or 3 of the physiological and morphological characteristics of variety NUN 11802 WMW (e.g., as listed in Tables 1-3).

In still another aspect, the disclosure provides a method of producing a watermelon plant, comprising crossing a plant of variety NUN 11802 WMW with a second watermelon plant at least once, allowing seed to develop and optionally harvesting said progeny seed. The skilled person can select progeny from said crossing. Optionally, the progeny (grown from the progeny seed) is crossed twice, thrice, or four, five, six or seven times, and allowed to set seed. In one aspect, the first "crossing" further comprises planting seeds of a first and a second parent watermelon plant, often in proximity so that pollination will occur; for example, mediated by insect vectors. Alternatively, pollen can be transferred manually. Where the plant is self-pollinated, pollination may occur without the need for direct human intervention other than plant cultivation. After pollination the plant can produce seed.

The disclosure also provides a method for collecting pollen of watermelon variety NUN 11802 WMW, comprising collecting pollen from a variety NUN 11802 WMW plant. Alternatively, the method comprises growing a watermelon variety NUN 11802 WMW plant until at least one flower contains pollen and collecting the pollen. In a particular aspect, the pollen is collected when it is mature or ripe. A suitable method for collecting pollen comprises collecting anthers or the part of the anther that contains pollen, for example, by cutting the anther or the part of the anther off. Pollen can be collected in a container. Optionally, collected pollen can be used to pollinate a watermelon flower.

In yet another aspect, the disclosure provides a method of producing a plant, comprising selfing a watermelon variety NUN 11802 WMW plant one or more times, and selecting a progeny plant from said selfing. In one aspect, the progeny plant retains all or all but one, two or three of the physiological and morphological characteristics of variety NUN 11802 WMW described above when grown under the same environmental conditions. In a different aspect, the progeny plant comprises all of the physiological and morphological characteristic of variety NUN 11802 WMW of Tables 1-3.

The disclosure also provides a method for developing a watermelon plant in a watermelon breeding program, using variety NUN 11802 WMW, or its parts as a source of plant breeding material. Suitable plant breeding techniques are recurrent selection, backcrossing, pedigree breeding, mass selection, mutation breeding and/or genetic marker enhanced selection. In one aspect, the method comprises crossing watermelon variety NUN 11802 WMW or its progeny, or a plant comprising all but 1, 2, or 3 or more of the morphological and physiological characteristics of variety NUN 11802 WMW (e.g., as listed in Tables 1-3), with a different watermelon plant, and wherein one or more offspring of the crossing are subject to one or more plant breeding techniques: recurrent selection, backcrossing, pedigree breeding, mass selection, mutation breeding and genetic marker enhanced selection (see, e.g., Vidaysky and Czosnek, (1998) Phytopathology 88(9): 910-4). For breeding methods in general, see, e.g., Principles of Plant Genetics and Breeding, 2007, George Acquaah, Blackwell Publishing, ISBN-13: 978-1-4051-3646-4.

In one aspect, pedigree selection is used as a breeding method for developing a watermelon variety. Pedigree selection is also known as the "Vilmorin System of Selection," see, e.g., Allard, John Wiley & Sons, Inc., 1999, pp. 64-67. In general, selection is first practiced among F2 plants. In the next season, the most desirable F3 lines are first identified, then desirable F3 plants within each line are selected. The following season and in all subsequent generations of inbreeding, the most desirable families are identified first, then desirable lines within the selected families are chosen. A family refers to lines that were derived from plants selected from the same progeny from the preceding generation.

Thus, progeny in connection with pedigree selection are either the generation (seeds) produced from the first cross (F1) or selfing (51), or any further generation produced by crossing and/or selfing (F2, F3, etc.) and/or backcrossing (BC1, BC2, etc.) one or more selected plants of the F1 and/or 51 and/or BC1 generation (or plants of any further generation, e.g., F2) with another watermelon plant (and/or with a wild relative of watermelon). Progeny may have all the physiological and morphological characteristics of watermelon variety NUN 11802 WMW when grown under the same environmental conditions and/or progeny may have (be selected for having) one or more of the distinguishing characteristics of watermelon variety NUN 11802 WMW.

In yet another aspect, the disclosure provides for a method of producing a new watermelon plant comprising crossing a plant of variety NUN 11802 WMW, or a plant comprising all but one, two, or three of the morphological and physiological characteristics of watermelon variety NUN 11802 WMW (as listed in Tables 1-3), or a progeny plant thereof, either as male or as female parent, with a second watermelon plant (or a wild relative of watermelon) one or more times, and/or selfing watermelon plant variety NUN 11802 WMW, or a progeny plant thereof, one or more time, and selecting a progeny watermelon plant from said crossing and/or selfing. The second watermelon plant may, for example, be a line or variety of the species *Citrullus lanatus*, or other *Citrullus* species or even other Cucurbitacea species.

In a further aspect, watermelon variety NUN 11802 WMW is used in crosses with other, different, watermelon varieties to produce first generation (F1) watermelon hybrid seeds and plants with superior characteristics. In a particular aspect, the disclosure provides a watermelon seed and a plant produced by crossing a first parent watermelon plant with a second parent watermelon plant, wherein at least one of the first or second parent watermelon plant is watermelon variety NUN 11802 WMW. In another aspect, the watermelon seed and plant produced are the first filial generation (F1) watermelon seed and plants produced by crossing the plant of watermelon variety NUN 11802 WMW with another watermelon plant.

The morphological and physiological characteristics of watermelon variety NUN 11802 WMW are provided in Tables 1-3, as collected in a trial according to USDA and/or UPOV standards. Encompassed herein is also a plant obtainable from watermelon variety NUN 11802 WMW (e.g., by selfing and/or crossing and/or backcrossing with said variety and/or progeny of said variety) comprising all or all but one, two, or three of the physiological and morphological characteristics of watermelon variety NUN 11802 WMW listed in Tables 1-3 (as determined at the 5% significance level for quantitative characteristics or identical for non-quantitative characteristics) when grown under the same environmental conditions and/or comprising one or more (or all; or all except one, two, or three) characteristics when grown under the same environmental conditions. The morphological and/or physiological characteristics may vary somewhat with variation in the environment (e.g., temperature, light intensity, day length, humidity, soil, fertilizer use, disease vectors), which is why a comparison under the same environmental conditions is preferred. Colors can best be measured using the Royal Horticultural Society (RHS) Chart.

In another aspect, the disclosure provides a method of producing a plant derived from a watermelon variety NUN 11802 WMW, comprising crossing a plant of variety NUN 11802 WMW either as a male or female parent with a second plant or selfing watermelon variety NUN 11802 WMW or vegetative reproduction of watermelon variety NUN 11802 WMW and collecting seeds from said crossing or selfing or regenerating a whole plant from the vegetable cell-or tissue culture. Also provided are seeds and/or plants obtained by this method. All plants produced using watermelon variety NUN 11802 WMW as a parent are within the scope of the disclosure including plant parts derived from watermelon variety NUN 11802 WMW.

In a further aspect, the method comprises growing a progeny plant of a subsequent generation and crossing the progeny plant of a subsequent generation with itself or a second plant and repeating the steps for additional 3-10 generations to produce a plant derived from watermelon variety NUN 11802 WMW. The plant derived from watermelon variety NUN 11802 WMW may be an inbred line and the aforementioned repeating crossing steps may be defined as comprising sufficient inbreeding to produce the inbred line. By selecting plants having one or more desirable traits of the line as well as potentially other selected traits.

The disclosure provides for methods of producing a plant which retain all the morphological and physiological characteristics of the plant described herein. The disclosure also provides for methods of producing a plant comprising all but 1, 2, or 3 or more of the morphological and physiological characteristics of watermelon variety NUN 11802 WMW (e.g., as listed in Tables 1-3), but which are still genetically closely related to said variety. The relatedness can, for example, be determined by fingerprinting techniques (e.g., making use of isozyme markers and/or molecular markers such as Single-nucleotide polymorphism (SNP) markers, amplified fragment length polymorphism (AFLP) markers, microsatellites, minisatellites, Random Amplified Polymorphic DNA (RAPD) markers, restriction fragment length polymorphism (RFLP) markers and others). A plant is "closely related" to variety NUN 11802 WMW if its DNA fingerprint is at least 80%, 90%, 95% or 98% identical to the fingerprint of said variety. In a particular aspect AFLP markers are used for DNA fingerprinting (see, e.g., Vos et al. 1995, Nucleic Acid Research 23: 4407-4414). A closely related plant may have a Jaccard's Similarity index of at least about 0.8, preferably at least about 0.9, 0.95, 0.98 or more (see, e.g., Parvathaneni et al., J. Crop Sci. Biotech. 2011 (March) 14 (1): 39-43). The disclosure also provides a plant obtained or selected by applying these methods on watermelon variety NUN 11802 WMW. Such a plant may be produced by traditional breeding techniques, or mutation or transformation or in another aspect, a plant may simply be identified and selected amongst plants of said variety, or progeny of said variety, e.g., by identifying a variant of watermelon variety NUN 11802 WMW, or within progeny of said variety, which variant differs from the variety described herein watermelon in one, two or three of the morphological and/or physiological characteristics (e.g., characteristics listed in Tables 1-3). In one aspect, the disclosure provides a watermelon plant having a Jaccard's Similarity index with watermelon variety NUN 11802 WMW of at least 0.8, e.g., at least 0.85, 0.9, 0.95, 0.98 or even at least 0.99.

In some aspects, the disclosure provides a watermelon plant comprising genomic DNA having at least 95%, 96%, 97%, 98% or 99% sequence identity compared to the genomic DNA sequence of a plant of variety NUN 11802 WMW as deposited under Accession Number NCIMB 43701. In some aspects, the watermelon plant further comprises all or all but 1, 2, or 3 of the morphological and physiological characteristics of variety NUN 11802 WMW (e.g., as listed in Tables 1-3). In other aspects, the watermelon plant is a hybrid derived from a seed or plant of variety NUN 11802 WMW. In other aspects, the watermelon plant further comprises all of the distinguishing characteristics of a plant of variety NUN 11802 WMW.

For the purpose of this disclosure, the "sequence identity" of nucleotide sequences, expressed as a percentage, refers to the number of positions in the two optimally aligned sequences which have identical residues (×100) divided by the number of positions compared. A gap, i.e., a position in the pairwise alignment where a residue is present in one sequence but not in the other, is regarded as a position with non-identical residues. A pairwise global sequence alignment of two nucleotide sequences is found by aligning the two sequences over the entire length according to the Needleman and Wunsch global alignment algorithm described in Needleman and Wunsch, 1970, J. Mol. Biol. 48(3):443-53). A full implementation of the Needleman-Wunsch global alignment algorithm is found in the needle program in The European Molecular Biology Open Software Suite (see, e.g., EMBOSS, Rice et al., Trends in Genetics June 2000, vol. 16, No. 6. pp. 276-277).

In another aspect, the plant of variety NUN 11802 WMW may also be mutated (by e.g., irradiation, chemical mutagenesis, heat treatment, etc.) and mutated seeds or plants may be selected in order to change one or more characteristics of said variety. Methods such as TILLING (Targeting Induced Local Lesions in Genomes) may be applied to populations in order to identify mutants.

Similarly, watermelon variety NUN 11802 WMW may be transformed and regenerated, whereby one or more chimeric genes are introduced into the variety or into a plant comprising all but 1, 2, 3, or more of the morphological and physiological characteristics (e.g., as listed in Tables 1-3). Many useful traits can be introduced into watermelon variety NUN 11802 WMW by e.g., crossing a watermelon variety NUN 11802 WMW with a transgenic watermelon plant comprising a desired transgene, as well as by directly introducing a transgene into watermelon variety NUN 11802 WMW by genetic transformation techniques.

Any pest or disease resistance genes may be introduced into watermelon variety NUN 11802 WMW, progeny of said variety or into a plant comprising all but 1, 2, or 3 or more of the morphological and physiological characteristics of variety NUN 11802 WMW (e.g., as listed in Tables 1-3). Resistance to one or more of the following diseases or pests may be introduced into plants described herein: *Colletotrichum orbiculare* (Anthracnose), *Pseudoperonospora cubensis* (Downy Mildew), *Fusarium oxysporum* f. sp. *niveum* (*Fusarium* Wilt), *Didymella bryoniae* (Gummy Stem Blight), *Podosphaera xanthii* (Powdery Mildew), *Verticillium* sp. (*Verticillium* Wilt), Squash Mosaic Virus, Watermelon Mosaic Virus (WMV), Cucumber Mosaic Virus (CMV), *Papaya* Ringspot Virus (PRWV-W), Zucchini Yellow Mosaic Virus (ZYMV), Cucurbit Yellow Stunting Disorder Virus (CYSDV), *Macrophomina phaseolina* (Charcoal Rot), *Monosporascus cannonballus* (*Monosporascus* Vine Decline), Sunburn, Root Knot, and/or *Bemisia tabaci* (Silverleaf Whitefly). Other resistance genes, against pathogenic viruses, fungi, bacteria, nematodes, insects or other pests may also be introduced.

Genetic transformation may, therefore, be used to insert a selected transgene into the watermelon plants of the disclosure described herein or may, alternatively, be used for the preparation of transgenic watermelon plants which can be used as a source of the transgene(s), which can be introduced into watermelon variety NUN 11802 WMW by e.g., backcrossing. A genetic trait which has been engineered into the genome of a particular watermelon plant may then be moved into the genome of another watermelon plant (e.g., another variety) using traditional breeding techniques which are well-known in the art. For example, backcrossing is commonly used to move a transgene from a transformed watermelon variety into an already developed watermelon variety and the resulting backcross conversion plant will then comprise the transgene(s).

Any DNA sequences, whether from a different species or from the same species, which are inserted into the genome using transformation, are referred to herein collectively as "transgenes." A "transgene" also encompasses antisense, or sense and antisense sequences capable of gene silencing. Thus, the disclosure also relates to transgenic plants of watermelon variety NUN 11802 WMW. In some aspects, a transgenic plant of watermelon variety NUN 11802 WMW may contain at least one transgene but could also contain at least 1, 2, 3, 4, or more transgenes.

Plant transformation involves the construction of an expression vector which will function in plant cells. Such a vector comprises DNA comprising a gene under control of, or operatively linked to a regulatory element active in plant cells (e.g., promoter). The expression vector may contain one or more such operably linked gene/regulatory element combinations. The vector may be in the form of a plasmid and can be used alone or in combination with other plasmids to provide transformed watermelon plants using transformation methods to incorporate transgenes into the genetic material of the watermelon plant(s). Transformation can be carried out using standard methods, such as *Agrobacterium tumefaciens* mediated transformation, electroporation, biolistics particle delivery system, or microprojectile bombardment, followed by selection of the transformed cells and regeneration into plants.

Plants can also be genetically engineered, modified, or manipulated to express various phenotypes of horticultural interest. Through the transformation of watermelon, the expression of genes can be altered to enhance disease resistance, insect resistance, herbicide resistance, stress tolerance, horticultural quality, and other traits. Transformation can also be used to insert DNA sequences which control or help control male sterility or fertility restoration. DNA sequences native to watermelon as well as non-native DNA sequences can be transformed into watermelon and used to alter levels of native or non-native proteins. Various promoters, targeting sequences, enhancing sequences, and other DNA sequences can be inserted into the genome for the purpose of altering the expression of proteins. Reduction of the specific activity of specific genes (also known as gene silencing or gene suppression) is desirable for several aspects of genetic engineering in plants.

Genome editing is another method recently developed to genetically engineer plants. Specific modification of chromosomal loci or targeted mutation can be done through sequence-specific nucleases (SSNs) by introducing a targeted DNA double strand break in the locus to be altered. Examples of SSNs that have been applied to plants are: finger nucleases (ZFNs), transcription activator-like effector nucleases (TALENs), engineered homing endonucleases or meganucleases, and clustered regularly interspaced short palindromic repeats (CRISPR)/CRISPR-associated protein 9 (Cas9), see, e.g., Songstad, et. al., Critical Reviews in Plant Sciences, 2017, 36:1, 1-23.

Thus, the disclosure also provides a method of producing a watermelon plant having a desired trait comprising mutating the plant or plant part of watermelon variety NUN 11802 WMW and selecting a plant comprising the desired trait, wherein the mutated plant retains all or all but one, two, or three of the morphological and physiological characteristics of variety NUN 11802 WMW, and contains the desired trait and wherein a representative sample of seed of said watermelon variety has been deposited under Accession Number NCIMB 43701. In a further aspect, the transformation or mutation confers a trait wherein the trait is yield, storage properties, color, flavor, male sterility, herbicide tolerance, insect resistance, pest resistance, disease resistance, environmental stress tolerance, modified carbohydrate metabolism, modified protein metabolism, or occurs in the intense gene.

The disclosure also provides a method for inducing a mutation in watermelon variety NUN 11802 WMW comprising:
a. exposing the seed, plant, plant part, or cell of watermelon variety NUN 11802 WMW to a mutagenic compound or to radiation, wherein a representative sample of seed of said watermelon variety NUN 11802 WMW has been deposited under Accession Number NCIMB 43701;
b. selecting the seed, plant, plant part, or cell of watermelon variety NUN 11802 WMW having a mutation; and
c. optionally growing and/or multiplying the seed, plant or plant part or cell of watermelon variety NUN 11802 WMW having the mutation.

The disclosure also provides a method of producing a watermelon plant having a desired trait, wherein the method comprises transforming the watermelon plant with a transgene that confers the desired trait, wherein the transformed plant otherwise retains all of the physiological and morphological characteristics of the plant of variety NUN 11802 WMW and contains the desired trait. Thus, a transgenic watermelon plant is provided which is produced by the method described above, wherein the plant otherwise has all of the physiological and morphological characteristics of watermelon variety NUN 11802 WMW and the desired trait.

In another aspect, the disclosure provides a method of producing a progeny of plant of variety NUN 11802 WMW further comprising a desired trait, said method comprising transforming the plant of watermelon variety NUN 11802 WMW with at least one transgene that confers the desired trait and/or crossing the plant of watermelon variety NUN 11802 WMW with a transgenic watermelon plant comprising a desired transgene so that the genetic material of the progeny that resulted from the cross contains the desired transgene(s). Also encompassed is the progeny produced by this method.

A desired trait (e.g., gene(s) conferring pest or disease resistance, or tolerance for protection, etc.) can be introduced into watermelon variety NUN 11802 WMW, or progeny of said variety, by transforming said variety or progeny of said variety with a transgene that confers the desired trait, wherein the transformed plant retains all or all but one, two or three of the morphological and/or physiological characteristics of variety NUN 11802 WMW and contains the desired trait. In another aspect, the transformation or mutation confers a trait wherein the trait is yield, storage properties, color, flavor, male sterility, herbicide tolerance, insect resistance, pest resistance, disease resistance, environmental stress tolerance, modified carbohydrate metabolism, modified protein metabolism or occurs in the intense gene. In a particular aspect, the specific transgene may be any known in the art or listed herein, including, a polynucleotide sequence conferring resistance to imidazolinone, sulfonylurea, glyphosate, glufosinate, triazine, benzonitrile, cyclohexanedione, phenoxy proprionic acid and L-phosphinothricin or a polynucleotide conferring resistance *Colletotrichum orbiculare* (Anthracnose), *Pseudoperonospora cubensis* (Downy Mildew), *Fusarium oxysporum* f. sp. *niveum* (*Fusarium* Wilt), *Didymella bryoniae* (Gummy Stem Blight), *Podosphaera xanthii* (Powdery Mildew), *Verticillium* sp. (*Verticillium* Wilt), Squash Mosaic Virus, Watermelon Mosaic Virus (WMV), Cucumber Mosaic Virus (CMV), *Papaya* Ringspot Virus (PRWV-W), Zucchini Yellow Mosaic Virus (ZYMV), Cucurbit Yellow Stunting Disorder Virus (CYSDV), *Macrophomina phaseolina* (Charcoal Rot), *Monosporascus cannonballus* (*Monosporascus* Vine Decline), Sunburn, Root Knot, and/or *Bemisia tabaci* (Silverleaf Whitefly). Other resistance genes, against pathogenic viruses, fungi, bacteria, nematodes, insects or other pests may also be introduced.

By crossing and/or selfing, (one or more) single traits may be introduced into watermelon variety NUN 11802 WMW (e.g., using backcrossing breeding schemes), while retaining the remaining morphological and physiological characteristics of said variety and/or while retaining one or more or all distinguishing characteristics. A single trait converted plant may thereby be produced. For example, disease resistance genes may be introduced, genes responsible for one or more quality traits, yield, etc. Both single genes (e.g., dominant or recessive) and one or more QTLs (quantitative trait loci) may be transferred into watermelon variety NUN 11802 WMW by breeding with said variety.

In another aspect, the disclosure provides a method of introducing a single locus conversion or single trait conversion or a desired trait into watermelon variety NUN 11802 WMW, comprising introducing a single locus conversion in at least one of the parents of variety NUN 11802 WMW; and crossing the converted parent with the other parent of variety NUN 11802 WMW, to obtain seed of said variety.

In another aspect, the step of introducing a single locus conversion, single trait conversion, or desired trait in at least one of the parent plants comprises:
a. crossing the parental line of watermelon variety NUN 11802 WMW with a second watermelon plant comprising the single locus conversion, the single trait conversion or the desired trait;
b. selecting F1 progeny plants that contain the single locus conversion, the single trait conversion or the desired trait;
c. crossing said selected progeny plants of step b) with the parental line of step a), to produce a backcross progeny plant;
d. selecting backcross progeny plants comprising the single locus conversion, the single trait conversion or the desired trait and otherwise all or all but one, two or three of the morphological and physiological characteristics the parental line of step a) to produce selected backcross progeny plants; and
e. optionally repeating steps c) and d) one or more times in succession to produce selected second, third or fourth or higher backcross progeny plants comprising the single locus conversion, the single trait conversion or the desired trait and otherwise all or all but one, two or three of the morphological and physiological characteristics the parental line of step a) to produce selected backcross progeny plants, when grown in the same environmental conditions.

The disclosure further relates to plants obtained by this method.

In another aspect, introducing a single locus conversion in at least one of the parent plants comprises:
a. obtaining a cell or tissue culture of cells of the parental line of watermelon variety NUN 11802 WMW;
b. genetically transforming or mutating said cells;
c. growing the cells into a plant; and
d. optionally selecting plants that contain the single locus conversion, the single trait conversion or the desired trait.

In another aspect, the disclosure provides a method of introducing a single locus conversion or single trait conversion or a desired trait into watermelon variety NUN 11802 WMW comprising:
a. obtaining a combination of a parental lines of watermelon variety NUN 11802 WMW, optionally through reverse synthesis of breeding lines;
b. introducing a single locus conversion in at least one of the parents of step a; and
c. crossing the converted parent with the other parent of step a to obtain seed of watermelon variety NUN 11802 WMW.

In another method, the step of introducing a single locus conversion in at least one of the parents comprises genetically transforming or mutating cells the parental line of watermelon variety NUN 11802 WMW; growing the cells into a plant; and optionally selecting plants that contain the single locus conversion, the single trait conversion or the desired trait.

In any of the above methods, where the single locus conversion concerns a trait, the trait may be yield or pest resistance or disease resistance. In one aspect, the trait is disease resistance and the resistance is conferred to *Colletotrichum orbiculare* (Anthracnose), *Pseudoperonospora cubensis* (Downy Mildew), *Fusarium oxysporum* f. sp. *niveum* (Fusarium Wilt), *Didymella bryoniae* (Gummy Stem Blight), *Podosphaera xanthii* (Powdery Mildew), *Verticillium* sp. (*Verticillium* Wilt), Squash Mosaic Virus, Watermelon Mosaic Virus (WMV), Cucumber Mosaic Virus (CMV), *Papaya* Ringspot Virus (PRWV-W), Zucchini Yellow Mosaic Virus (ZYMV), Cucurbit Yellow Stunting Disorder Virus (CYSDV), *Macrophomina phaseolina* (Charcoal Rot), *Monosporascus cannonballus* (*Monosporascus* Vine Decline), Sunburn, Root Knot, and/or *Bemisia tabaci* (Silverleaf Whitefly). Other resistance genes against pathogenic viruses, fungi, bacteria, nematodes, insects or other pests may also be introduced.

The disclosure also provides a plant having one, two, or three physiological and/or morphological characteristics which are different from those of watermelon variety NUN 11802 WMW and which otherwise has all the physiological and morphological characteristics of said variety, wherein a representative sample of seed of said variety has been deposited under Accession Number NCIMB 43701. In particular, variants which differ from watermelon variety NUN 11802 WMW in no, one, two, or three of the characteristics mentioned in Tables 1-3 are encompassed.

The disclosure also provides a plant comprising at least a first set of the chromosomes of watermelon variety NUN 11802 WMW, a sample of seed has been deposited under Accession Number NCIMB 43701, optionally further comprising a single locus conversion. In another aspect, the single locus conversion confers a trait wherein the trait is yield, storage, color, flavor, male sterility, herbicide tolerance, insect resistance, pest resistance, disease resistance, environmental stress tolerance, modified carbohydrate metabolism, modified protein metabolism, or ripening.

In another aspect, the disclosure provides a haploid plant and/or a doubled haploid plant of variety NUN 11802 WMW, or a plant having all but one, two, or three physiological and/or morphological characteristics of variety NUN 11802 WMW, or progeny of any of these. Haploid and doubled haploid (DH) plants can, for example, be produced by cell or tissue culture and chromosome doubling agents and regeneration into a whole plant. DH production chromosome doubling may be induced using known methods, such as colchicine treatment or the like. In one aspect, the method comprises inducing a cell or tissue culture with a chromosome doubling agent and regenerating the cells or tissues into a whole plant.

In another aspect, the disclosure comprises a method for making doubled haploid cells of watermelon variety NUN 11802 WMW, comprising making doubled haploid cells from haploid cells from the plant or plant part of watermelon variety NUN 11802 WMW with a chromosome doubling agent such as colchicine treatment (see, e.g., Nikolova and Niemirowicz-Szczytt (1996) Acta Soc Bot Pol 65:311-317).

In yet another aspect, the disclosure provides for haploid plants and/or doubled haploid plants derived from watermelon variety NUN 11802 WMW that, when combined, make a set of parents of variety NUN 11802 WMW. The haploid plant and/or the doubled haploid plant of variety NUN 11802 WMW can be used in a method for generating parental lines of watermelon variety NUN 11802 WMW.

The disclosure also provides methods for determining the identity of parental lines of plants described herein, in particular the identity of the female line. US2015/0126380, which is hereby incorporated by reference, relates to a non-destructive method for analyzing maternal DNA of a seed. In this method, the DNA is dislodged from the seed coat surface and can be used to collect information on the genome of the maternal parent of the seed. This method for analyzing maternal DNA of a seed comprises contacting a seed with a fluid to dislodge DNA from the seed coat surface, and analyzing the DNA thus dislodged from the seed coat surface using methods known in the art. The skilled person is thus able to determine whether a seed has grown on a plant of a plant of variety NUN 11802 WMW or is a progeny of said variety, because the seed coat of the seed is a maternal tissue genetically identical to variety NUN 11802 WMW. In one aspect, the disclosure relates to a maternal tissue of variety NUN 11802 WMW. In another aspect, the disclosure relates to a watermelon seed comprising a maternal tissue of variety NUN 11802 WMW. In another particular aspect, the disclosure provides a method of identifying the female parental line of watermelon variety NUN 11802 WMW by analyzing the seed coat of a seed of that variety. In another aspect, the skilled person can determine whether a seed is grown on watermelon NUN 11802 WMW by analyzing the seed coat or another maternal tissue of said seed.

Using methods known in the art such as "reverse synthesis of breeding lines" or "reverse breeding", it is possible to produce parental lines for a hybrid plant such as watermelon variety NUN 11802 WMW. A skilled person can take any individual heterozygous plant (called a "phenotypically superior plant" in Example 2 of US2015/0245570 hereby incorporated by reference in its entirety; watermelon variety NUN 11802 WMW is such a plant) and generate a combination of parental lines (reverse breeding parental lines) that, when crossed, produce the variety NUN 11802 WMW. It is not necessary that the reverse breeding parental lines are identical to the original parental lines. Such new breeding methods are based on the segregation of individual alleles in the spores produced by a desired plant and/or in the progeny derived from the self-pollination of that desired plant, and on the subsequent identification of suitable progeny plants in one generation, or in a limited number of inbred cycles. Such a method is known from US2015/0245570 or from Wijnker et al., Nature Protocols Volume: 9, Pages: 761-772 (2014) DOI: doi:10.1038/nprot.2014.049. Thus, the disclosure provides a method for producing parental lines for a hybrid organism (e.g., watermelon variety NUN 11802 WMW), comprising in one aspect: a) defining a set of genetic markers present in a heterozygous form (H) in a partially heterozygous starting organism; b) producing doubled haploid lines from spores of the starting organism; c) genetically characterizing the doubled haploid lines thus obtained for the said set of genetic markers to determine whether they are present in a first homozygous form (A) or in a second homozygous form (B); and d) selecting at least one pair of doubled haploid lines that have complementary alleles for at least a subset of the genetic markers, wherein each member of the pair is suitable as a parental line for the hybrid organism.

In another aspect, the method for producing parental lines for hybrid organisms, e.g., of NUN 11802 WMW, which when crossed reconstitute the genome of NUN 11802 WMW, comprising:
  a. defining a set of genetic markers that are present in a first homozygous form (H) in a partially heterozygous starting organism;
  b. producing at least one further generation from the starting organism by self-pollination (e.g., F2 or F3 generation);
  c. selecting at least one pair of progeny organisms in which at least one genetic marker from the set is present in a complementary homozygous forms (B vs. A, or A vs. B); and
  d. optionally repeating steps b) and c) until at least one pair of progeny organisms that have complementary alleles for at least a subset of the genetic markers has been selected as parental lines for a hybrid.

The disclosure relates to a method of producing a combination of parental lines of a plant of variety NUN 11802 WMW, comprising making doubled haploid cells from haploid cells from said plant or a seed of that plant; and optionally crossing these parental lines to produce and collecting seeds. In another aspect, the disclosure relates to a combination of parental lines produced by this method. In still another aspect, the combination of parental lines can be used to produce a seed or plant of variety NUN 11802 WMW when these parental lines are crossed. In still another aspect, the disclosure relates to a combination of parental lines from which a seed or plant having all physiological and/or morphological characteristics of variety NUN 11802 WMW (when the characteristics are determined at the 5% significance level for plants grown under the same environmental conditions).

The disclosure also provides a combination of parental lines which, when crossed, produce a seed or plant having all physiological and/or morphological characteristics of watermelon variety NUN 11802 WMW but one, two or three characteristics which are different (when grown under the same environmental conditions), as well as a seed or plant having all physiological and/or morphological characteristics of variety NUN 11802 WMW but one, two or three characteristics which are different (when the characteristics are determined at the 5% significance level for plants grown under the same environmental conditions).

In another aspect, a combination of a male and a female parental line of watermelon variety NUN 11802 WMW can be generated by methods described herein, for example, through reverse synthesis of breeding lines.

In another aspect, the disclosure provides a method of determining the genotype of a plant described herein comprising detecting in the genome (e.g., a sample of nucleic acids) of the plant at least a first polymorphism or an allele. The skilled person is familiar with many suitable methods of genotyping, detecting a polymorphism or detecting an allele including SNP (Single Nucleotide Polymorphism) genotyping, restriction fragment length polymorphism identification (RFLP) of genomic DNA, random amplified polymorphic detection (RAPD) of genomic DNA, amplified fragment length polymorphism detection (AFLP), polymerase chain reaction (PCR), DNA sequencing, allele specific oligonucleotide (ASO) probes, and hybridization to DNA microarrays or beads. Alternatively, the entire genome could be sequenced. The method may, in certain embodiments, comprise detecting a plurality of polymorphisms in the genome of the plant, for example by obtaining a sample of nucleic acid from a plant and detecting in said nucleic acids a plurality of polymorphisms. The method may further comprise storing the results of the step of detecting the plurality of polymorphisms on a computer readable medium.

Also provided is a plant part of variety NUN 11802 WMW (or from progeny of said variety or from a plant having all physiological and/or morphological characteristics but one, two, or three which are different from those of said variety) or from a vegetatively propagated plant of variety NUN 11802 WMW (or from its progeny or from a plant having all or all but one, two, or three of the physiological and morphological characteristics which are different from those of watermelon variety NUN 11802 WMW), wherein said plant part is a fruit, a harvested fruit, a part of a fruit, a leaf, a part of a leaf, pollen, an ovule, a cell, a petiole, a shoot or a part thereof, a stem or a part thereof, a root or a part thereof, a root tip, a cutting, a seed, a part of a seed, seed coat or another maternal tissue which is part of a seed grown on said variety, a hypocotyl, cotyledon, a scion, a stock, a rootstock, a pistil, an anther, and a flower or a part thereof.

A part of the plant of variety NUN 11802 WMW (or of progeny of said variety or of a plant having all of the physiological and morphological characteristics but one, two, or three which are different from those of said variety) encompasses any cells, tissues, organs obtainable from the seedlings or plants, such as but not limited to: a watermelon fruit or a part thereof, a cutting, a hypocotyl, a cotyledon, seed coat, or pollen.

Such a plant part of variety NUN 11802 WMW can be stored and/or processed further. The disclosure thus also provides for a food or feed product comprising one or more of such parts from watermelon variety NUN 11802 WMW or from progeny of said variety, or from a derived variety, such as a plant having all but one, two, or three physiological and/or morphological characteristics of variety NUN 11802 WMW. Preferably, the plant part is a watermelon fruit or part thereof and/or an extract from a fruit or another plant part described herein comprising at least one cell of watermelon variety NUN 11802 WMW. The food or feed product may be fresh or processed, e.g., dried, grinded, powdered, pickled, chopped, cooked, roasted, in a sauce, in a sandwich, pasted, puréed or concentrated, juiced, pickled, canned, steamed, boiled, fried, blanched and/or frozen, etc.

In another aspect, the disclosure provides for a watermelon fruit of variety NUN 11802 WMW, or a part of a fruit of said variety. The fruit can be in any stage of maturity, for example, immature or mature. In another aspect, the disclosure provides for a container comprising or consisting of a plurality of harvested watermelon fruits or parts of fruits of said variety, or fruits of progeny thereof, or fruits of a derived variety.

Marketable fruits are generally sorted by size and quality after harvest. Alternatively, the fruits can be sorted by expected shelf life, pH or Brix.

In another aspect, the plant, plant part or seed of watermelon variety NUN 11802 WMW is inside a container, for example, containers such as cans, boxes, crates, bags, cartons, Modified Atmosphere Packaging, films (e.g., biodegradable films), etc. comprising a plant or a plant part (fresh and/or processed) or a seed of watermelon variety NUN 11802 WMW. In a particular aspect, the container comprises a plurality of seeds, or a plurality of plant parts of watermelon variety NUN 11802 WMW.

In another aspect, a seed or a plurality of seeds of said variety are packaged into a container of any size or type (e.g., bags, cartons, cans, etc.) The seed may be disinfected, primed and/or treated with various compounds, such as seed coatings or crop protection compounds. The seed produces a plant of variety NUN 11802 WMW.

Watermelons may also be grown for use as rootstocks (stocks) or scions. Typically, different types of watermelons are grafted to enhance disease resistance, which is usually conferred by the rootstock, while retaining the horticultural qualities usually conferred by the scion. It is not uncommon for grafting to occur between cultivated watermelon varieties and related watermelon species. Methods of grafting and vegetative propagation are well-known in the art.

In another aspect, the disclosure provides to a plant comprising a rootstock or scion of watermelon variety NUN 11802 WMW.

All documents (e.g., patent publications) are herein incorporated by reference in their entirety, including the following cited references:

Naktuinbouw, Calibration Manual: DUS Test for Watermelon (*Citrullus lanatus*), 2017.

UPOV, Guidelines for the Conduct of Tests for Distinctness, Uniformity and Stability, TG142/5, world-wide web at upov.int/edocs/tgdocs/en/tg142.pdf.

US Department of Agriculture, Objective Description of Variety—Watermelon (*Citrullus lanatus*)", world-wide web at ams.usda.gov/under services/plant-variety-protection/pvpo-c-forms under watermelon.

Compton, M., et al., "Use of Tissue Culture and Biotechnology for the Genetic Improvement of Watermelon", Plant Cell, Tissue and Organ Culture, 2004, vol. 77, pp. 231-243.

Eigsti, O., "About our Cover", HortScience, 1971, vol. 6, pp. 1-2.

Hayata, Y., et. al., "Synthetic Cytokinin-1-(2=chloro=4=pyridyl)-3-phenylurea (CPPU)-Promotes Fruit Set and Induces Parthenocarpy in Watermelon", Society of Horticultural Science, 1995, vol. 120(6), pp. 997-1000.

Kihara, H., "Triploid Watermelon", Proceedings of American Society for Horticultural Science, 1951, vol. 58, pp. 217-230.

Moussa, H., et. al., "Parthenocarpy of Watermelon Cultivars Induced by γ-Irradiation", Russian Journal of Plant Physiology, 2010, vol. 57, no. 4, pp. 574-581.

Parvathaneni, R. K., et al., "Fingerprinting in Cucumber and Melon (*Cucumis* spp.) genotypes Using Morphological and ISSR Markers", Journal of Crop Science and Biotechnology, 2011, vol. 14, no. 1, pp. 39-43. DOI No. 10.1007/s12892-010-0080-1.

Rice, P., et al., "EMBOSS: The European Molecular Biology Open Software Suite", Trends in Genetics, 2000, vol. 16, Issue 6. pp. 276-277.

Vidaysky, F., et. al., "Tomato Breeding Lines Resistant and Tolerant to Tomato Yellow Leaf Curl Virus Issued from *Lycopersicum hirsutum*", The American Phytopathology Society, 1998, vol. 88, no. 9, pp. 910-914.

Vos, P., et al., "AFLP: A New Technique for DNA Fingerprinting", Nucleic Acids Research, 1995, vol. 23(21), pp. 4407-4414.

Wijnker, E., et al., "Hybrid Recreation by Reverse breeding in *Arabidopsis thaliana*", Nature Protocols, 2014, vol. 9, pp. 761-772. DOI: doi: 10.1038/nprot.2014.049

U.S. Pat. No. 8,418,637
US2015/0126380
US2015/0245570
US2006/0168701

Development of Watermelon Variety NUN 11802 WMW

The hybrid NUN 11802 WMW was developed from a male and female proprietary inbred line of Nunhems. The female and male parents were crossed to produce hybrid (F1) seeds of watermelon variety NUN 11802 WMW. The seeds of watermelon variety NUN 11802 WMW can be grown to produce hybrid plants and parts thereof (e.g., watermelon fruit). The hybrid watermelon variety NUN 11802 WMW can be propagated by seeds or vegetatively.

The hybrid variety is uniform and genetically stable. This has been established through evaluation of horticultural characteristics. Several hybrid seed production events resulted in no observable deviation in genetic stability. Coupled with the confirmation of genetic stability of the female and male parents the Applicant has concluded that watermelon variety NUN 11802 WMW is uniform and stable.

Deposit Information

A total of 2500 seeds of the hybrid variety NUN 11802 WMW has been deposited according to the Budapest Treaty by Nunhems B.V. on Dec. 15, 2020 at the NCIMB Ltd., Ferguson Building, Craibstone Estate, Bucksburn, Aberdeen AB21 9YA, United Kingdom (NCIMB). The deposit has been assigned NCIMB Number 43701. A statement indicating the viability of the sample has been provided. A deposit of watermelon variety NUN 11802 WMW and of the male and female parent line is also maintained at Nunhems B.V. The seed lot number for watermelon variety NUN 11802 WMW is 28766701006.

The deposit will be maintained in NCIMB for a period of 30 years, or 5 years after the most recent request, or for the enforceable life of the patent whichever is longer and will be replaced if it ever becomes nonviable during that period. Access to the deposits will be available during the pendency of this application to persons determined by the Director of the U.S. Patent Office to be entitled thereto upon request. Subject to 37 C.F.R. § 1.808(b), all restrictions imposed by the depositor on the availability to the public of the deposited material will be irrevocably removed upon the granting of the patent. Applicant does not waive any rights granted under this patent on this application or under the Plant Variety Protection Act (7 U.S.C. § 2321 et seq.) Accordingly, the requirements of 37 CFR § 1.801-1.809 have been satisfied.

Characteristics of Watermelon Variety NUN 11802 WMW

The most similar variety to NUN 11802 WMW refers to variety NUN 4001 WM, a variety from Nunhems B.V., with the commercial name Premium.

In Table 1, the characteristics of watermelon variety NUN 11802 WMW is shown based on a trial in Italy. For numerical characteristics, averages were calculated. For non-numerical characteristics, the type/degree were determined.

In Tables 2 and 3, a comparison between watermelon variety NUN 11802 WMW and the Reference variety is shown based on a trial in the USA. Trial location: Esparto, California, USA; Seeding date: May 11, 2021; Transplanting date: Jun. 15, 2021; Harvesting date: Aug. 25, 2021. In Table 4, the distinguishing characteristics between watermelon variety NUN 11802 WMW and the Reference Variety are shown.

One replication of 20 plants per variety, from which at least 15 plants or plant parts were randomly selected and were used to measure characteristics. For numerical characteristics, averages were calculated. For non-numerical characteristics, the type/degree were determined. Similarity and differences between two different plant lines or varieties can be determined by comparing the number of morphological and/or physiological characteristics (e.g., characteristics as listed in Tables 1 and 2) that are the same (i.e., statistically not significantly different) or that are different (i.e., statistically significantly different) between the two plant lines or varieties using plants grown under the same environmental conditions. A numerical characteristic is considered to be "the same" when the value for a numeric characteristic is not significantly different at the 1% (p<0.01) or 5% (p<0.05) significance level, using T-test, a standard method known to the skilled person. A non-numerical or "degree" or "type" characteristic is considered "the same" when the values have the same "degree" or "type" when scored using USDA and/or UPOV descriptors, for plants are grown under the same environmental conditions. In one aspect, a statistical analysis using the T-Test at 5% significance level is provided (see, Tables 5-19).

In one aspect, the disclosure provides a watermelon plant having the physiological and morphological characteristics of watermelon variety NUN 11802 WMW as presented in Tables 1-3 when grown under the same environmental conditions.

TABLE 1

Objective description of watermelon variety NUN 11802 WMW, Italy

| Characteristics | Application Variety (NUN 11802 WMW) |
| --- | --- |
| General Fruit Type: | |
| Fruit type: oblong, round large, round small (icebox), other | Round oval, small |
| Maturity: | |
| Days relative maturity: | 60 days after transplanting |
| Maturity category: early, medium, late | Early |
| Ploidy: | |
| diploid, tetrapioid, triploid | Diploid |
| Plant: | |
| Plant sex form: monoecious, andromonoecious | Monoecious |
| Plant vigor: | Low |
| Mature Fruit: | |
| Fruit shape: round, oval, cylindrical | Round oval |
| Primary color: | Green |
| Fruit surface: smooth, slightly grooved, deeply grooved | Smooth |
| Skin color pattern: solid (one color), stripe, mottle/Net | Stripe |
| Rind: | |
| Rind texture: tender, brittle, tough | Tender |
| Flesh: | |
| Flesh texture: | Soft |

TABLE 1-continued

Objective description of watermelon variety NUN 11802 WMW, Italy

| Characteristics | Application Variety (NUN 11802 WMW) |
|---|---|
| crisp, soft | |
| Flesh coarseness: | Fine |
| course fibrous, fine (little fiber) | |
| Flesh color: | Red |
| white, yellow, orange, pink, red, dark red | |
| Resistance: | |
| Fusarium oxysporum f. sp. niveum Race 0 | Highly resistant |
| Fusarium oxysporum f. sp. niveum Race 1 | Highly resistant |

TABLE 2

Objective Description of Watermelon Variety NUN 11802 WMW and Reference Variety (USDA Descriptors)

| Characteristics | Application Variety (NUN 11802 WMW) | Reference Variety (NUN 4001 WM) |
|---|---|---|
| General Fruit Type: | | |
| Fruit type: | Round small | Round large |
| oblong, round large, round small (icebox), other | | |
| Ploidy: | | |
| diploid, tetraploid, triploid | Diploid | Diploid |
| Plant: | | |
| Plant sex form: monoecious, andromonoecious | Monoecious | NR |
| Stem: | | |
| Stem shape (cross section:) | Angular | Angular |
| round, angular | | |
| Diameter at second node (mm): | 10.68 mm | 8.18 mm |
| Stem surface: | Scabrous | Scabrous |
| glabrous, scabrous, pubescent, bristled | | |
| Leaf: | | |
| Leaf shape: | Ovate | Ovate |
| Ovate, Obovate, Round | | |
| Leaf lobes: | Lobed | Lobed |
| None; Lobed | | |
| Leaf length (cm): | 12.57 cm | 13.98 cm |
| Leaf width (cm): | 10.57 cm | 12.19 cm |
| Leaf size: | Longer than wide | Longer than wide |
| longer than wide, length-width equal, wider than long | | |
| Dorsal surface pubescence: | Pubescent | Pubescent |
| smooth, pubescent | | |
| Ventral surface pubescence: | Pubescent | Pubescent |
| smooth, pubescent | | |
| Leaf color: | Gray green RHS 191A | Dark green RHS 189A |
| light green, gray green, medium green, dark green | | |
| Mature Fruit: | | |
| Fruit shape: | Oval | Oval |
| round, oval, cylindrical | | |
| Long (cm): | 18.73 cm | 21.60 cm |
| Diameter at midsection (cm): | 16.39 cm | 17.96 cm |
| Average weight (kg): | 2,578.40 g | 3,465.73 g |
| Maximum fruit weight (kg): | 2,8782.0 g | 4,676.0 g |
| Index = length ÷ diameter × 10 (fruit shape index): | 11.42 | 12.03 |
| Fruit surface: | Smooth | Smooth |
| smooth, slightly grooved, deeply grooved | | |
| Skin color pattern: | Stripe | Stripe |
| solid (one color), stripe, mottle/net | | |
| Primary color (ground color): | Light green RHS 193A | Light green RHS 145C |
| Secondary color (stripes): | Dark green RHS N189A | Dark green RHS 139A |
| Rind: | | |
| Rind texture: | Tender | NR |
| tender, brittle, tough | | |
| Thickness at blossom end (mm): | 4.96 mm | 4.42 mm |
| Thickness at sides (mm): | 6.84 mm | 6.61 mm |
| Flesh: | | |
| Flesh texture: | Soft | NR |
| crisp, soft | | |
| Flesh color: | Red RHS 179B | Red RHS 179B |
| Refractometer: % Soluble solids of juice (Center of fruit) | 10.13% | 11.31% |
| Resistance: | | |
| Fusarium oxysporum f. sp. niveum Race 0 | Highly resistant | Intermediately Resistant |
| Fusarium oxysporum f. sp. niveum Race 1 | Highly resistant | Intermediately Resistant |

TABLE 3

Objective Description of Watermelon Variety NUN 11802 WMW and the Reference Variety (Non-USDA Descriptors)

| Characteristics | Application Variety (NUN 11802 WMW) | Reference Variety (NUN 4001 WM) |
|---|---|---|
| Leaf: | | |
| Leaf blade - length of the 3$^{rd}$ leaf when fully developed: short, medium, long | Medium | Medium |
| Leaf blade size: small, medium, large | Medium | Medium |
| Leaf blade - ratio length/wide: small, medium, large | Medium | Medium |
| Leaf blade - color: | Greyish green | Green |
| Leaf blade - degree of lobing: absent or very weak, very weak to weak, weak, weak to medium, medium, medium to strong, strong, strong to very strong, very strong | Strong | Strong |
| Leaf blade- blistering (on 10$^{th}$ to 15$^{th}$ leaf): weak, medium, strong | Weak | Weak |
| Leaf blade- color of veins: green, yellow | Green | Green |
| Leaf petiole length (cm): | 10.71 cm | 12.79 cm |
| Leaf petiole width (cm): | 3.91 cm | 4.60 cm |
| Leaf length/width index: | 1.19 | 1.15 |
| Mature fruit: | | |
| Fruit shape in longitudinal section: circular, broad elliptic, medium elliptic, narrow elliptic | Broad elliptic | Medium elliptic |
| Depression at base: absent or very shallow, shallow, medium deep, | Shallow | Shallow |

TABLE 3-continued

Objective Description of Watermelon Variety NUN 11802
WMW and the Reference Variety (Non-USDA Descriptors)

| Characteristics | Application Variety (NUN 11802 WMW) | Reference Variety (NUN 4001 WM) |
|---|---|---|
| very deep | | |
| Shape of apical part: truncate, truncate to rounded, rounded, rounded to acute, acute | Rounded | Rounded |
| Depression at apex: absent or very weak, weak, shallow, medium, deep, very deep | Absent or very shallow | Absent or very shallow |
| Conspicuousness of veining: inconspicuousness of very weakly conspicuous, weak, medium, strong, very strong | Weak | Medium |
| Pattern of stripes: only one color, one color and veins, one colored, veins and marbled, one colored and marbled, two colored, veins and marbled, only veins | One colored and marbled | Colored, veins, and marbled |
| Size of insertion of peduncle: small, medium, large | Medium | Medium |
| Shape at basal part: | Rounded | Rounded |
| Size of pistil scar: small, medium, large | Medium | Medium |
| Grooving: absent or very weak, weak, medium, strong | Absent or very weak | Absent or very weak |
| Waxy layer: absent or very weak, weak, medium, strong | Absent or very weak | Absent or very weak |
| Stripes: absent, present | Present | Present |
| Margin of stripes: diffuse, medium, sharp | Sharp | Sharp |
| Intensity of color of stripes: | Dark | Dark |
| Width of stripes: very narrow, very narrow to narrow, narrow, narrow to medium, medium, medium to broad, broad, broad to very broad | Narrow | Narrow |
| Main color of stripes: | Dark green | Dark green |
| Conspicuousness of stripes: inconspicuousness of very weakly conspicuous, weak, medium, strong, very strong | Strong | Strong |
| Thickness of pericarp: Very thin, Thin, Medium, Thick, Very thick | Thin | Thin |
| Peduncle length, mm: | 41.02 mm | 49.94 mm |
| Peduncle width, mm: | 7.13 mm | 7.91 mm |
| Rind: | | |
| Thickness at stem end (mm): | 9.11 mm | 10.74 mm |
| Flesh: | | |
| Penetrometer (kg): | 2.17 kg | 1.83 kg |

TABLE 4

Distinguishing Characteristics between Watermelon
Variety NUN 11802 WMW and the Reference Variety

| Characteristics | Application Variety (NUN 11802 WMW) | Reference Variety (NUN 4001 WM) |
|---|---|---|
| Fruit type: oblong, round large, round small (icebox), other | Round small | Round large |
| Stem: | | |
| Diameter at second node (mm): | 10.68 mm | 8.18 mm |
| Leaf: | | |
| Leaf length (cm): | 12.57 cm | 13.98 cm |
| Leaf width (cm): | 10.57 cm | 12.19 cm |
| Leaf color: light green, gray green, medium green, dark green | Gray green RHS 191A | Dark green RHS 189A |
| Leaf petiole length (cm): | 10.71 cm | 12.79 cm |
| Leaf petiole width (cm): | 3.91 cm | 4.60 cm |
| Mature fruit: | | |
| Long (cm): | 18.73 cm | 21.60 cm |
| Diameter at midsection (cm): | 16.39 cm | 17.96 cm |
| Average weight (kg): | 2,578.40 g | 3,465.73 kg |
| Primary color (ground color): | Light green RHS 193A | Light green RHS 145C |
| Secondary color (stripes): | Dark green RHS N189A | Dark green RHS 139A |
| Fruit shape in longitudinal section: circular, broad elliptic, medium elliptic, narrow elliptic | Broad elliptic | Medium elliptic |
| Conspicuousness of veining: inconspicuousness of very weakly conspicuous, weak, medium, strong, very strong | Weak | Medium |
| Pattern of stripes: only one color, one color and veins, one colored, veins and marbled, one colored and marbled, two colored, veins and marbled, only veins | One colored and marbled | Colored, veins, and marbled |
| Peduncle length, mm: | 41.02 mm | 49.94 mm |
| Peduncle width, mm: | 7.13 mm | 7.91 mm |
| Rind: | | |
| Thickness at stem end (mm): | 9.11 mm | 10.74 mm |
| Flesh: | | |
| Refractometer: % Soluble solids of juice (Center of fruit) | 10.13% | 11.31% |

The results of the T-Test show significant differences between watermelon variety NUN 11802 WMW and the Reference Variety for the diameter at second node, leaf length, leaf width, petiole length, petiole width, fruit length, fruit diameter, fruit weight, peduncle length, peduncle width, thickness at stem end, and % soluble solids of juice as shown in Tables 5-16.

Table 5 shows a significant difference between watermelon variety NUN 11802 WMW and the Reference Variety ($p<0.001$) on diameter at second node (mm) based on the results of the trial conducted in the US during the trial season 2021.

TABLE 5

| Statistical Parameters | Application Variety (NUN 11802 WMW) | Reference Variety (NUN 4001 WM) |
|---|---|---|
| No. of samples | 15 | 15 |
| Min. | 7.18 | 6.75 |
| Max. | 14.84 | 10.60 |

TABLE 5-continued

| Statistical Parameters | Application Variety (NUN 11802 WMW) | Reference Variety (NUN 4001 WM) |
|---|---|---|
| Median | 10.40 | 8.0 |
| Mean | 10.68 | 8.18 |
| Standard deviation | 1.92 | 1.10 |

Table 6 shows a significant difference between watermelon variety NUN 11802 WMW and the Reference Variety (p=0.001) on leaf length (cm) based on the results of the trial conducted in the US during the trial season 2021.

TABLE 6

| Statistical Parameters | Application Variety (NUN 11802 WMW) | Reference Variety (NUN 4001 WM) |
|---|---|---|
| No. of samples | 15 | 15 |
| Min. | 10.60 | 11.80 |
| Max. | 14.0 | 16.0 |
| Median | 12.90 | 14.30 |
| Mean | 12.57 | 13.98 |
| Standard deviation | 0.91 | 1.21 |

Table 7 shows a significant difference between watermelon variety NUN 11802 WMW and the Reference Variety (p<0.001) on leaf width (cm) based on the results of the trial conducted in the US during the trial season 2021.

TABLE 7

| Statistical Parameters | Application Variety (NUN 11802 WMW) | Reference Variety (NUN 4001 WM) |
|---|---|---|
| No. of samples | 15 | 15 |
| Min. | 9.40 | 10.60 |
| Max. | 12.90 | 14.40 |
| Median | 10.40 | 12.0 |
| Mean | 10.57 | 12.19 |
| Standard deviation | 0.91 | 1.16 |

Table 8 shows a significant difference between watermelon variety NUN 11802 WMW and the Reference Variety (p<0.001) on petiole length (cm) based on the results of the trial conducted in the US during the trial season 2021.

TABLE 8

| Statistical Parameters | Application Variety (NUN 11802 WMW) | Reference Variety (NUN 4001 WM) |
|---|---|---|
| No. of samples | 15 | 15 |
| Min. | 9.0 | 10.80 |
| Max. | 13.70 | 16.0 |
| Median | 10.80 | 12.30 |
| Mean | 10.71 | 12.79 |
| Standard deviation | 1.29 | 1.51 |

Table 9 shows a significant difference between watermelon variety NUN 11802 WMW and the Reference Variety (p<0.001) on petiole width (cm) based on the results of the trial conducted in the US during the trial season 2021.

TABLE 9

| Statistical Parameters | Application Variety (NUN 11802 WMW) | Reference Variety (NUN 4001 WM) |
|---|---|---|
| No. of samples | 15 | 15 |
| Min. | 3.30 | 3.90 |
| Max. | 4.58 | 5.60 |

TABLE 9-continued

| Statistical Parameters | Application Variety (NUN 11802 WMW) | Reference Variety (NUN 4001 WM) |
|---|---|---|
| Median | 3.92 | 4.38 |
| Mean | 3.91 | 4.60 |
| Standard deviation | 0.34 | 0.53 |

Table 10 shows a significant difference between watermelon variety NUN 11802 WMW and the Reference Variety (p<0.001) on fruit length (cm) based on the results of the trial conducted in the US during the trial season 2021.

TABLE 10

| Statistical Parameters | Application Variety (NUN 11802 WMW) | Reference Variety (NUN 4001 WM) |
|---|---|---|
| No. of samples | 15 | 15 |
| Min. | 17.10 | 18.70 |
| Max. | 19.80 | 24.20 |
| Median | 18.60 | 21.70 |
| Mean | 18.73 | 21.60 |
| Standard deviation | 0.83 | 1.74 |

Table 11 shows a significant difference between watermelon variety NUN 11802 WMW and the Reference Variety (p<0.001) on fruit diameter (cm) based on the results of the trial conducted in the US during the trial season 2021.

TABLE 11

| Statistical Parameters | Application Variety (NUN 11802 WMW) | Reference Variety (NUN 4001 WM) |
|---|---|---|
| No. of samples | 15 | 15 |
| Min. | 15.40 | 16.0 |
| Max. | 17.30 | 19.80 |
| Median | 16.20 | 17.70 |
| Mean | 16.39 | 17.96 |
| Standard deviation | 0.53 | 1.13 |

Table 12 shows a significant difference between watermelon variety NUN 11802 WMW and the Reference Variety (p<0.001) on fruit weight (g) based on the results of the trial conducted in the US during the trial season 2021.

TABLE 12

| Statistical Parameters | Application Variety (NUN 11802 WMW) | Reference Variety (NUN 4001 WM) |
|---|---|---|
| No. of samples | 15 | 15 |
| Min. | 2,046.0 | 2,402.0 |
| Max. | 2,872.0 | 4,676.0 |
| Median | 2,560.0 | 3,400.0 |
| Mean | 2,578.40 | 3,465.73 |
| Standard deviation | 253.29 | 668.40 |

Table 13 shows a significant difference between watermelon variety NUN 11802 WMW and the Reference Variety (p=0.003) on peduncle length (mm) based on the results of the trial conducted in the US during the trial season 2021.

TABLE 10

| Statistical Parameters | Application Variety (NUN 11802 WMW) | Reference Variety (NUN 4001 WM) |
|---|---|---|
| No. of samples | 15 | 15 |
| Min. | 32.25 | 34.63 |
| Max. | 52.21 | 70.52 |

TABLE 10-continued

| Statistical Parameters | Application Variety (NUN 11802 WMW) | Reference Variety (NUN 4001 WM) |
|---|---|---|
| Median | 39.55 | 48.07 |
| Mean | 41.02 | 49.94 |
| Standard deviation | 6.02 | 8.93 |

Table 14 shows a significant difference between watermelon variety NUN 11802 WMW and the Reference Variety (p=0.001) on peduncle width (mm) based on the results of the trial conducted in the US during the trial season 2021.

TABLE 14

| Statistical Parameters | Application Variety (NUN 11802 WMW) | Reference Variety (NUN 4001 WM) |
|---|---|---|
| No. of samples | 15 | 15 |
| Min. | 6.54 | 6.87 |
| Max. | 8.17 | 8.75 |
| Median | 7.0 | 7.84 |
| Mean | 7.13 | 7.91 |
| Standard deviation | 0.43 | 0.63 |

Table 15 shows a significant difference between watermelon variety NUN 11802 WMW and the Reference Variety (p=0.008) on thickness at stem end (mm) based on the results of the trial conducted in the US during the trial season 2021.

TABLE 15

| Statistical Parameters | Application Variety (NUN 11802 WMW) | Reference Variety (NUN 4001 WM) |
|---|---|---|
| No. of samples | 15 | 15 |
| Min. | 6.09 | 7.55 |
| Max. | 12.13 | 13.54 |
| Median | 9.33 | 11.03 |
| Mean | 9.11 | 10.74 |
| Standard deviation | 1.59 | 1.56 |

Table 16 shows a significant difference between watermelon variety NUN 11802 WMW and the Reference Variety (p<0.001) on % soluble solids of juice based on the results of the trial conducted in the US during the trial season 2021.

TABLE 16

| Statistical Parameters | Application Variety (NUN 11802 WMW) | Reference Variety (NUN 4001 WM) |
|---|---|---|
| No. of samples | 15 | 15 |
| Min. | 8.90 | 10.10 |
| Max. | 10.90 | 12.10 |
| Median | 10.10 | 11.40 |
| Mean | 10.13 | 11.31 |
| Standard deviation | 0.53 | 0.55 |

The results of the T-test show no significant differences between watermelon variety NUN 11802 WMW and the Reference Variety for thickness at blossom end, thickness at side, and penetrometer reading as shown in Tables 17-19.

Table 17 shows no significant difference between watermelon variety NUN 11802 WMW and the Reference Variety (p=0.244) on thickness at blossom end (mm) based on the results of the trial conducted in the US during the trial season 2021.

TABLE 17

| Statistical Parameters | Application Variety (NUN 11802 WMW) | Reference Variety (NUN 4001 WM) |
|---|---|---|
| No. of samples | 15 | 15 |
| Min. | 2.19 | 2.53 |
| Max. | 6.98 | 6.97 |
| Median | 5.23 | 4.14 |
| Mean | 4.96 | 4.42 |
| Standard deviation | 1.21 | 1.30 |

Table 18 shows no significant difference between watermelon variety NUN 11802 WMW and the Reference Variety (p=0.669) on thickness at side (mm) based on the results of the trial conducted in the US during the trial season 2021.

TABLE 18

| Statistical Parameters | Application Variety (NUN 11802 WMW) | Reference Variety (NUN 4001 WM) |
|---|---|---|
| No. of samples | 15 | 15 |
| Min. | 3.92 | 4.11 |
| Max. | 10.99 | 8.39 |
| Median | 6.60 | 6.69 |
| Mean | 6.84 | 6.61 |
| Standard deviation | 1.58 | 1.37 |

Table 19 shows no significant difference between watermelon variety NUN 11802 WMW and the Reference Variety (p=0.080) on penetrometer reading (kg) based on the results of the trial conducted in the US during the trial season 2021.

TABLE 19

| Statistical Parameters | Application Variety (NUN 11802 WMW) | Reference Variety (NUN 4001 WM) |
|---|---|---|
| No. of samples | 15 | 15 |
| Min. | 1.50 | 1.30 |
| Max. | 3.50 | 3.0 |
| Median | 2.0 | 1.80 |
| Mean | 2.17 | 1.83 |
| Standard deviation | 0.57 | 0.47 |

The invention claimed is:

1. A plant or seed of watermelon variety NUN 11802 WMW, wherein a representative sample of seed of said watermelon variety has been deposited under Accession Number NCIMB 43701.

2. A plant part of the plant of claim 1, wherein said plant part is a leaf, a fruit, a scion, a root, a rootstock, or a cutting.

3. A seed that produces the plant of claim 1.

4. A plant or part thereof grown from the seed of claim 1.

5. A watermelon plant, or a part thereof having all the physiological and morphological characteristics of the plant of claim 1 or part thereof when grown under the same environmental conditions.

6. A watermelon plant, or a part thereof obtained from the plant of claim 1, which does not differ in any of the physiological and morphological characteristics of watermelon variety NUN 11802 WMW, when the numerical characteristics are determined at the 5% significance level and identical for non-numerical characteristics when grown under the same environmental conditions, and wherein a representative sample of seed of said watermelon variety NUN 11802 WMW has been deposited under Accession Number NCIMB 43701.

7. A tissue or cell culture comprising regenerable cells of the plant of claim 1, said cells are obtained from watermelon variety NUN 11802 WMW and are suitable for regeneration into a plant having all of the morphological and physiological characteristics of watermelon variety NUN 11802 WMW.

8. The tissue or cell culture according to claim 7, comprising cells or protoplasts obtained from a plant part suitable for vegetative reproduction, wherein the plant part is a meristem, a cotyledon, a hypocotyl, a leaf, an anther, a root, a root tip, a pistil, a petiole, a flower, a fruit, a stem, or a stalk.

9. A watermelon plant regenerated from the tissue or cell culture of claim 7, wherein the plant has all of the physiological and morphological characteristics of the plant of variety NUN 11802 WMW.

10. A method of producing the plant of claim 1 or part thereof, said method comprising vegetatively propagating at least a part of the plant of watermelon variety NUN 11802 WMW, wherein a representative sample of seed of said watermelon variety has been deposited under Accession Number NCIMB 43701.

11. The method of claim 10, wherein said vegetative propagating comprises regenerating a whole plant from a part of the plant of variety NUN 11802 WMW, wherein a representative sample of seed of said watermelon variety has been deposited under Accession Number NCIMB 43701.

12. The method of claim 10, wherein said part is a cutting, a cell culture, or a tissue culture.

13. A vegetatively propagated plant or part thereof produced by the method of claim 10, wherein the plant has all of the physiological and morphological characteristics of the plant of variety NUN 11802 WMW, when the numerical characteristics are determined at the 5% significance level and identical for non-numerical characteristics for plants grown under the same environmental conditions, and wherein a representative sample of seed of watermelon variety has been deposited under Accession Number NCIMB 43701.

14. A method of producing a watermelon plant, said method comprising crossing the plant of claim 1 with a second watermelon plant at least once, selecting a progeny watermelon plant from said crossing and optionally allowing the progeny to form seed.

15. A method of producing a watermelon seed, said method comprising crossing watermelon plants and harvesting the resultant seed, wherein at least one watermelon plant is the plant of claim 1, and wherein a representative sample of seed of said watermelon variety NUN 11802 WMW has been deposited under Accession Number NCIMB 43701.

16. A method of introducing a single locus conversion into the plant of claim 1, comprising:
  a. crossing the plant of claim 1 with a second watermelon plant comprising a desired single locus conversion to produce F1 progeny plants;
  b. selecting F1 progeny plants that have the single locus conversion to produce selected F1 progeny plants;
  c. crossing selected F1 progeny plants with watermelon variety NUN 11802 WMW to produce backcross progeny plants;
  d. selecting backcross progeny plants that have the single locus conversion and otherwise comprise all of the physiological and morphological characteristics of the watermelon variety NUN 11802 WMW to produce selected backcross progeny plants; and
  e. repeating steps (c) and (d) one or more times in succession to produce selected second or higher backcross progeny plants that comprise the single locus conversion and otherwise comprise all of the physiological and morphological characteristics of the watermelon variety NUN 11802 WMW, wherein a representative sample of seed of said watermelon variety has been deposited under Accession Number NCIMB 43701.

17. The method of claim 16, wherein the single locus conversion confers male sterility, herbicide tolerance, insect resistance, pest resistance, disease resistance, environmental stress tolerance, modified carbohydrate metabolism, or modified protein metabolism.

18. A watermelon plant produced by the method of claim 16, wherein the plant comprises the single locus conversion and otherwise has all of the physiological and morphological characteristics of the plant of watermelon variety NUN 11802 WMW.

19. A method of introducing a desired trait into the plant of claim 1, said method comprising transforming the plant of claim 1 with a transgene that confers the desired trait, wherein the desired trait is male sterility, herbicide tolerance, insect resistance, pest resistance, disease resistance, environmental stress tolerance, modified carbohydrate metabolism, or modified protein metabolism.

20. A watermelon plant produced by the method of claim 19, wherein the transformed plant contains the desired trait and otherwise has all of the physiological and morphological characteristics of watermelon variety NUN 11802 WMW.

21. A method of making doubled haploid cells of the plant of claim 1, said method comprising making doubled haploid cells from haploid cells from the plant or plant part of watermelon variety NUN 11802 WMW, wherein a representative sample of seed of said watermelon variety has been deposited under Accession Number NCIMB 43701.

22. A method of grafting the scion or rootstock, comprising attaching a tissue from the scion or rootstock of claim 2 to the tissue of a second plant, and optionally regenerating a plant therefrom.

23. A plant comprising the scion or rootstock of claim 2.

24. A container comprising the plant or seed of claim 1.

25. A food product, a feed product, or a processed product comprising a plant part of watermelon variety NUN 11802 WMW, wherein the plant part comprises at least a regenerable cell of watermelon variety NUN 11802 WMW, and wherein a representative sample of seed of watermelon variety has been deposited under Accession Number NCIMB 43701.

26. A method of producing a modified watermelon plant having a desired trait, wherein the method comprises mutating the plant of claim 1 or part thereof, and selecting a plant with the desired trait, wherein the mutated plant contains the desired trait and otherwise retains all of the physiological and morphological characteristics of the plant of variety NUN 11802 WMW, when the numerical characteristics are determined at the 5% significance level and identical for non-numerical characteristics for plants grown under the same environmental conditions, wherein a representative sample of seed of said watermelon variety has been deposited under Accession Number NCIMB 43701, and wherein the desired trait is male sterility, herbicide tolerance, insect resistance, pest resistance, disease resistance, environmental stress tolerance, modified carbohydrate metabolism, or modified protein metabolism.

27. A method of producing a watermelon fruit, said method comprising growing the plant of claim 1 until it sets fruit; and collecting at least one fruit.

28. A fruit collected by the method of claim 27.

29. A container comprising the fruit collected by the method of claim 27.

30. A method for determining the genotype of the plant of claim 1, said method comprising obtaining a sample of nucleic acids from said plant, detecting in said nucleic acid a plurality of polymorphisms, thereby determining the genotype of the plant, and storing the results of detecting the plurality of polymorphisms on a computer readable medium.

31. A method of producing a watermelon plant obtained from the plant of claim 1, comprising:
   a. obtaining a progeny watermelon plant from watermelon variety NUN 11802 WMW by crossing the plant of claim 1 with itself or with a second watermelon plant;
   b. crossing the progeny plant with itself or a different watermelon plant to produce a seed of a progeny plant of a subsequent generation;
   c. growing a progeny plant of the subsequent generation from said seed and crossing the progeny plant of the subsequent generation with itself or another watermelon plant; and
   d. repeating steps (b) and (c) for a least one more generation to produce a watermelon plant obtained from watermelon variety NUN 11802 WMW.

32. A method for developing a watermelon plant in a watermelon breeding program, said method comprising applying plant breeding techniques selected from the group consisting of recurrent selection, backcrossing, mass selection, mutation breeding, genetic marker enhanced selection, and genetic transformation to the plant of claim 1 or part thereof, wherein said plant breeding techniques result in a development of a watermelon plant.

\* \* \* \* \*